US008642739B2

(12) United States Patent
Denefle et al.

(10) Patent No.: US 8,642,739 B2
(45) Date of Patent: Feb. 4, 2014

(54) NUCLEAR FACTOR κB INDUCING FACTOR

(75) Inventors: Patrice Denefle, Saint Maur (FR); Thomas F. Haws, Wilmington, DE (US); June M. Kaplow, Doylestown, PA (US); Marie Rosier, Antony (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 13/157,815

(22) Filed: Jun. 10, 2011

(65) Prior Publication Data
US 2011/0263831 A1 Oct. 27, 2011

Related U.S. Application Data

(60) Division of application No. 11/354,560, filed on Feb. 15, 2006, now Pat. No. 7,972,844, which is a continuation of application No. 09/823,119, filed on Mar. 30, 2001, now Pat. No. 7,041,497.

(60) Provisional application No. 60/193,905, filed on Mar. 31, 2000.

(30) Foreign Application Priority Data

Jul. 26, 2000 (GB) .................................. 0018307.9

(51) Int. Cl.
*C07K 14/00* (2006.01)
(52) U.S. Cl.
USPC ........................................ 530/387.9; 530/350
(58) Field of Classification Search
None
See application file for complete search history.

(56) References Cited

U.S. PATENT DOCUMENTS

| 4,650,764 | A | | 3/1987 | Temin et al. |
|---|---|---|---|---|
| 4,797,368 | A | | 1/1989 | Carter et al. |
| 4,861,719 | A | | 8/1989 | Miller |
| 4,980,289 | A | | 12/1990 | Temin et al. |
| 4,987,071 | A | | 1/1991 | Cech et al. |
| 5,124,263 | A | | 6/1992 | Temin et al. |
| 5,139,941 | A | | 8/1992 | Muzyczka et al. |
| 5,399,346 | A | | 3/1995 | Anderson et al. |
| 5,459,127 | A | | 10/1995 | Felgner et al. |
| 5,580,859 | A | | 12/1996 | Felgner et al. |
| 5,589,466 | A | | 12/1996 | Felgner et al. |
| 5,693,622 | A | | 12/1997 | Wolff et al. |
| 6,132,964 | A | * | 10/2000 | Bandman et al. .................. 435/6 |
| 6,518,029 | B1 | * | 2/2003 | Bandman et al. .............. 435/7.1 |
| 2011/0263831 | A1 | | 10/2011 | Kaplow et al. |

FOREIGN PATENT DOCUMENTS

| CA | 2012311 | | 3/1990 |
|---|---|---|---|
| EP | 0 140 308 | A2 | 5/1985 |
| EP | 0 178 220 | A2 | 4/1986 |
| EP | 0 185 573 | A1 | 6/1986 |
| EP | 0 453 242 | A1 | 10/1991 |
| EP | 0 488 528 | A1 | 6/1992 |
| FR | 1994 0013355 | | 10/1994 |
| WO | 89/07150 | A1 | 8/1989 |
| WO | 90/02806 | A1 | 3/1990 |
| WO | 91/18088 | A1 | 11/1991 |
| WO | 92/05263 | A1 | 4/1992 |
| WO | 92/15680 | A1 | 9/1992 |
| WO | 93/08845 | A1 | 5/1993 |
| WO | 93/09239 | A1 | 5/1993 |
| WO | 93/23569 | A1 | 11/1993 |
| WO | 94/02595 | A1 | 2/1994 |
| WO | 94/02610 | A1 | 2/1994 |
| WO | 94/12649 | A2 | 6/1994 |
| WO | 94/21807 | A2 | 9/1994 |
| WO | 94/26914 | A1 | 11/1994 |
| WO | 94/28152 | A1 | 12/1994 |
| WO | 94/28938 | A1 | 12/1994 |
| WO | 94/29446 | A2 | 12/1994 |
| WO | 95/02697 | A1 | 1/1995 |
| WO | 95/04064 | A1 | 2/1995 |
| WO | 95/07358 | A1 | 3/1995 |
| WO | 95/18863 | A1 | 7/1995 |
| WO | 95/21931 | A1 | 8/1995 |
| WO | 96/17823 | A1 | 6/1996 |
| WO | 96/22378 | A1 | 7/1996 |
| WO | 96/25508 | A1 | 8/1996 |
| WO | 99/58675 | A2 | 11/1999 |
| WO | 00/00599 | A2 | 1/2000 |
| WO | 01/31030 | A1 | 5/2001 |
| WO | 01/53312 | A1 | 7/2001 |
| WO | 01/77389 | A2 | 10/2001 |
| WO | 01/94629 | A2 | 12/2001 |

OTHER PUBLICATIONS

Bowie et al. (Science, 1990, 247:1306-1310).*
Burgess et al. (J. Cell Biol. 111:2129-2138, 1990).*

(Continued)

*Primary Examiner* — Brian J Gangle
*Assistant Examiner* — Andrea McCollum
(74) *Attorney, Agent, or Firm* — McDonnell Boehnen Hulbert & Berghoff LLP

(57) ABSTRACT

The present invention is directed to nuclear factor κB (NFκB)-inducing factor polypeptides (NFIF polypeptides) which are capable of inducing NFκB. The present invention includes within its scope NFIF polypeptides, including NFIF-14b and NFIF-7a, DNA, including cDNA, encoding these polypeptides, and expression vectors capable of expressing NFIF polypeptides. Also included are methods and compositions for increasing NFκB induction in a patient, methods and compositions for lowering NFκB induction in a patient, methods for inhibiting inflammation, and methods for manufacture of a medicament intended for the treatment and/or prevention of an NFκB-regulated inflammatory response. In addition, methods for determining whether a test compound inhibits or enhances the activity of NFIF polypeptides are provided.

9 Claims, 9 Drawing Sheets

(56) References Cited

OTHER PUBLICATIONS

Lazar et al. (Mol. Cell. Biol., 8:1247-1252, 1988).*
Bork (Genome Research, 2000,10:398-400).*
International Search Report from International Application No. PCT/US01/10719, mailed Mar. 8, 2002.
International Preliminary Examination Report in International Application No. PCT/US01/10719, report completed Jul. 12, 2002.
Adams et al., "The c-myc oncogene driven by immunoglobulin enhancers induces lymphoid malignancy in transgenic mice," 318(6046) Nature 533-38 (1985).
Alexander et al., "Expression of the c-myc oncogene under control of an immunoglobulin enhancer in E mu-myc transgenic mice," 7(4) Mol Cell Biol 1436-44 (1987).
Altschul et al., "Basic local alignment search tool," 215(3) J Mol Biol 403-10 (1990).
Altschul et al., "Gapped BLAST and PSI-BLAST: a new generation of protein database search programs," 25(17) Nucleic Acids Res 3389-402 (1997).
Aruffo (Kaufman), "Expression of Proteins in Mammalian Cells; Transient Expression of Proteins using COS Cells," in Current Protocols in Molecular Biology, vol. 3, Unit 16.12 (Ausubel et al., eds. 1998).
Beard et al., "Transcription mapping of mouse adenovirus type 1 early region 3," 175(1) Virology 81-90 (1990).
Bender et al., "Evidence that the packaging signal of Moloney murine leukemia virus extends into the gag region," 61 (5) J Virol 1639-46 (1987).
Benoist & Chambon, "In vivo sequence requirements of the SV40 early promotor region," 290(5804) Nature 304-310 (1981).
Bernstein et al., "Gene transfer with retrovirus vectors," in Genetic Engineering: Principles and Methods, vol. 7:235-61 (Setlow and Hollaender, eds. 1985).
Brinster et al., "Regulation of metallothionein—thymidine kinase fusion plasmids injected into mouse eggs," 296 (5852) Nature 39-42 (1982).
Chatterjee et al., "Sphingolipids in atherosclerosis and vascular biology," Arterioscler. Thromb. Vasc. Biol. 18:1523-33 (1988).
Chen et al., Multitarget-ribozyme directed to cleave at up to nine highly conserved HIV-1 env RNA regions inhibits HIV-1 replication—potential effectiveness against most presently sequenced HIV-1 isolates, 20(17) Nucleic Acids Res 4581-9 (1992).
Collins & Olive, Reaction conditions and kinetics of self-cleavage of a ribozyme derived from Neurospora VS RNA, 23(32) Biochemistry 2795-2799 (1993).
Curiel et al., High-efficiency gene transfer mediated by adenovirus coupled to DNA-polylysine complexes, 3(2) Hum Gene Ther 147-154 (1992).
De Boer, et al., "A flow- and time-dependent index of ischemic injury after experimental coronary occlusion and reperfusion," 80(18) Proc Nat'l Acad Sci USA 21-5 (1983).
Dias Neto et al., "Shotgun sequencing of the human transcriptome with ORF expressed sequence tags," Proc. Nat'l. Acad. Sci. U.S.A. 97(7):3491-96 (2000).
Dropulić et al., "Functional characterization of a U5 ribozyme: intracellular suppression of human immunodeficiency virus type 1 expression," 66(3) J Virol 1432-41 (1992).
Elroy-Stein & Moss, "Cytoplasmic expression system based on constitutive synthesis of bacteriophage T7 RNA polymerase in mammalian cells," 87(17) Proc Nat'l. Acad Sci USA 6743-7 (1990).
Felgner et al., "Lipofection: a highly efficient, lipid-mediated DNA-transfection procedure," 84(21) Proc Nat'l Acad Sci USA 7413-17 (1987).
Felgner & Ringold, "Cationic liposome-mediated transfection," 337(6205) Nature 387-88 (1989).
Fields et al., "HBTU activation for automated Fmoc solid-phase peptide synthesis," 4(2) Peptide Research 95-101 (1991).
Gao & Huang, "Cytoplasmic expression of a reporter gene by co-delivery of T7 RNA polymerase and T7 promoter sequence with cationic liposomes," 21(12) Nucleic Acids Res 2867-72 (1993).

Guerrier-Takada et al., "The RNA moiety of ribonuclease P is the catalytic subunit of the enzyme," 35(3 Pt 2) Cell 849-57 (1983).
Gius et al., "Intracellular oxidation/reduction status in the regulation of transcription factors NF-B and AP-1," Toxicology Letters, 106:93-106 (1999).
Graham, "Covalently closed circles of human adenovirus DNA are infectious," 3(12) EMBO J 2917-22 (1984).
Graham et al., "Characteristics of a human cell line transformed by DNA from human adenovirus type 5," 36(1) J Gen Viral 59-74 (1977).
Grosschedl et al., "Introduction of a mu immunoglobulin gene into the mouse germ line: specific expression in lymphoid cells and synthesis of functional antibody," 38(3) Cell 647-58 (1984).
Hammer et al., "Diversity of alpha-fetoprotein gene expression in mice is generated by a combination of separate enhancer elements," 235(4784) Science 53-8 (1987).
Hampel & Tritz, "RNA catalytic properties of the minimum (−)sTRSV sequence," 28(12) Biochemistry 4929-33 (1989).
Hampel et al., "'Hairpin' catalytic RNA model: evidence for helices and sequence requirement for substrate RNA," 18 (2) Nucleic Acids Res 299-304 (1990).
Hanahan, "Heritable formation of pancreatic beta-cell tumours in transgenic mice expressing recombinant insulin/simian virus 40 oncogenes," 315(6015) Nature 115-22 (1985).
Higuchi, "Using PCR to Engineer DNA," in PCR Technology: Principles and Applications for DNA Amplification, Chapter 6:61-70 (Erlich ed., 1989).
Hutchison et al., "A complete library of point substitution mutations in the glucocorticoid response element of mouse mammary tumor virus," 83(3) Proc Nat'l Acad Sci USA 710-4 (1986).
Hutchison et al., "Mutagenesis at a specific position in a DNA sequence," 253(18) J Biol Chem 6551-60 (1978).
Kaplitt et al., "Expression of a functional foreign gene in adult mammalian brain following in vivo transfer via a herpes simplex virus type 1 defective viral vector," 2(4) Mol Cell Neurosci 320-30 (1991).
Kashani-Sabet et al., "Reversal of the malignant phenotype by an anti-ras ribozyme," 2(1) Antisense Res Dev 3-15 (1992).
Kelsey et al., "Species- and tissue-specific expression of human alpha 1-antitrypsin in transgenic mice," 1(2) Genes and Dev 161-71 (1987).
Khaled et al., "Inhibition of the p50 (NFκB1) Subunit of NF-κB by Phosphorothioate-Modified Antisense Oligodeoxynucleotides Reduces NFκB Expression and Immunoglobulin Synthesis in Murine B Cells," Clin. Immunol. Immunopathol. 83(3):254-63 (1997).
King et al., "A cleavage method which minimizes side reactions following Fmoc solid phase peptide synthesis," 36(3) Int'l J Peptide and Protein Research 255-66 (1990).
Kollias et al., "Regulated expression of human A gamma-, beta-, and hybrid gamma beta-globin genes in transgenic mice: manipulation of the developmental expression patterns," 46(1) Cell 89-94 (1986).
Krumlauf et al., "Developmental regulation of alpha-fetoprotein genes in transgenic mice," 5(7) Mol Cell Biol 1639-48 (1985).
Kuo et al., "Efficient gene transfer into primary murine lymphocytes obviating the need for drug selection," 82(3) Blood 845-52 (1993).
Lebkowski et al., "Adeno-associated virus: a vector system for efficient introduction and integration of DNA into a variety of mammalian cell types," 8(10) Mol Cell Biol 3988-96 (1988).
Leder et al., "Consequences of widespread deregulation of the c-myc gene in transgenic mice: multiple neoplasms and normal development," 45(4) Cell 485-95 (1986).
Le Gal La Salle et al., "An adenovirus vector for gene transfer into neurons and glia in the brain," 259(5097) Science 988-90 (1993).
Lentsch at al., "Activation and regulation of NFkappaB during acute inflammation," Clin. Chem. Lab. Med. 37 (3):205-08 (1999).
Levade et al., "Signalling sphingomyelinases: which, where, how and why," Biochimica et Biophysica Acta 1438:1-17 (1999).
Levrero et al., "Defective and nondefective adenovirus vectors for expressing foreign genes in vitro and in vivo," 101 (2) Gene 195-202 (1991).
L'Huillier et al., "Cytoplasmic delivery of ribozymes leads to efficient reduction in alpha-lactalbumin mRNA levels in C127I mouse cells," 11(12) EMBO J 4411-8 (1992).
Li et al., "Regulation of NF-kappaB by the HTLV-1 Tax protein," Gene Expr. 7(4-6):233-45 (1999).

(56) References Cited

OTHER PUBLICATIONS

Lieber et al., "Stable high-level gene expression in mammalian cells by T7 phage RNA polymerase," 217 Methods Enzymol 47-66 (1993).
Lisziewicz et al., "Inhibition of human immunodeficiency virus type 1 replication by regulated expression of a polymeric Tat activation response RNA decoy as a strategy for gene therapy in AIDS," 90(17) Proc Nat'l Acad Sci USA 8000-4 (1993).
MacDonald, "Expression of the pancreatic elastase I gene in transgenic mice," 7(1 Suppl) Hepatology 42S-51S (1987).
Machy, et al., "Gene transfer from targeted liposomes to specific lymphoid cells by electroporation," 85(21) Proc Nat'l Acad Sci USA 8027-31 (1988).
Mallat et al., "Shed Membrane Microparticles with Procoagulant Potential in Human Atherosclerotic Plaques," Circulation 99:348-53 (1999).
Magram et al., "Developmental regulation of a cloned adult beta-globin gene in transgenic mice," 315(6017) Nature 338-40 (1985).
Mann et al., "Construction of a retrovirus packaging mutant and its use to produce helper-free defective retrovirus," Cell 153-9 (1983).
Markowitz et al., "A safe packaging line for gene transfer: separating viral genes on two different plasmids," 62(4) J Viral 1120-4 (1988).
Mason et al., "The hypogonadal mouse: reproductive functions restored by gene therapy," 234(4782) Science 1372-8 (1986).
McCormick, "Human Gene Therapy: The first round," 3(8) Bio/Technology 689-93 (1985).
Miller & Rosman, "Improved retroviral vectors for gene transfer and expression," 7 BioTechniques 980-90 (1992).
Morrissey et al., "Transcription factor NF-kappaB regulation of renal fibrosis during ureteral obstruction," Seminars and Nephrology 18(6):603-11 (1998).
Mukhopadhyay et al., "Identification and Characterization of a Novel Cytokine, THANK, a TNF Homologue That Activates Apoptosis, Nuclear Factor-kappaB, and c-Jun NH2-Terminal Kinase," J Biol Chem, 274(23):15978-81 (1999).
Mukhopadhyay et al., "Altered expression of the p50 subunit of the NF•kappa B transcription factor complex in non-small cell lung carcinorma," Oncogene 11(5):999-1003 (1995).
Murakami et al., "HTLV-1 Tax Enhances NF-κB2 Expression and Binds to the Products p52 and p100, but Does Not Suppress the Inhibitory Function of p100," Virology 206:1066-74 (1995).
Ohkawa et al., "Activities of HIV-RNA targeted riobozymes transcribed from a 'shot-gun' type ribozyme-trimming plasmid," Nucleic Acids Symposium Series, No. 27, 15-16 (1992).
Ojwang et al., "Inhibition of human immunodeficiency virus type 1 expression by a hairpin ribozyme," 89(22) Proc Nat'l Acad Sci USA 10802-6 (1992).
Oliphant et al., "Cloning of random-sequence oligodeoxynucleotides," 44(2-3) Gene 177-83 (1986).
Ornitz et al., "Elastase I promoter directs expression of human growth hormone and SV40 T antigen genes to pancreatic acinar cells in transgenic mice," 50 Cold Spring Harbor Symposia on Quantitative Biology, vol. 1:399-409 (1985).
Pahl, "Activators and target genes of Rel/NF-kappa B transcription Factors," Oncogene 18(49):6853-68 (1999).
Perrotta & Been, "Cleavage of oligoribonucleotides by a ribozyme derived from the hepatitis delta virus RNA sequence," 31(1) Biochemistry 16-21 (1992).
Piete et al., "Multiple redox regulation in NF-kappaB transcription factor activation," Biol. Chem. 378:1237-45 (1997).
Pinkert et al., "An albumin enhancer located 10 kb upstream functions along with its promoter to direct efficient, liver-specific expression in transgenic mice," 1(3) Genes and Dev 268-76 (1987).
Readhead et al., "Expression of a myelin basic protein gene in transgenic shiverer mice: correction of the dysmyelinating phenotype.," 48(4) Cell 703-12 (1987).
Reeck et al., ""Homology" in proteins and nucleic acids: a terminology muddle and a way out of it," 50(5) Cell 667 (1987).

Rossi et al., "Ribozymes as Anti-HIV-1 Therapeutic Agents: Principles, Applications, and Problems," AIDS Research and Human Retroviruses 183-9 (1992).
Samulski et al., "A recombinant plasmid from which an infectious adeno-associated virus genome can be excised in vitro and its use to study viral replication," 61 (10) J Viral 3096-101 (1987).
Samulski et al., "Helper-free stocks of recombinant adeno-associated viruses: normal integration does not require viral gene expression," 63(9) J Viral 3822-8 (1989).
Sarver et al., "Ribozymes as potential anti-HIV-1 therapeutic agents," 247(4947) Science 1222-5 (1990).
Saville & Collins, "A site-specific self-cleavage reaction performed by a novel RNA in *Neurospora* mitochondria," 61(4) Cell 685-96 (1990).
Saville & Collins, "RNA-mediated ligation of self-cleavage products of a *Neurospora* mitochondrial plasmid transcript," 88(19) Proc Nat'l Acad Sci USA 8826-30 (1991).
Scanlon et al., "Ribozyme-mediated cleavage of c-fos mRNA reduces gene expression of DNA synthesis enzymes and metallothionein," 88(23) Proc Nat'l Acad Sci USA 10591-5 (1991).
Schissel et al., "Zn2•stimulated Sphingomyelinase Is Secreted by Many Cell Types and Is a Product of the Acid Sphingomyelinase Gene," J. Biol. Chem. 271(31):18431-36 (1996).
Schuchman at al., "Human acid sphingomyelinase. Isolation, nucleotide sequence and expression of the full-length and alternatively spliced cDNAs," J. Biol. Chem. 266(13):8531-39 (1991).
Shani, "Tissue-specific expression of rat myosin light-chain 2 gene in transgenic mice," 314(6008) Nature 283-86 (1985).
Smith & Johnson, "Single-step purification of polypeptides expressed in *Escherichia coli* as fusions with glutathione S-transferase," 67(1) Gene 31-40 (1988).
Stockinger et al., "Molecular characterization and functional analysis of the leukocyte surface protein CD31," 145 (11) J Immunol 3889-97 (1990).
Stratford-Perricaudet et al. "Widespread long-term gene transfer to mouse skeletal muscles and heart," 90(2) J Clin Invest 626-30 (1992).
Sugano et al., *Homo sapiens* cDNA FLJ20177. Clone COL09966, highly similar to Y08136 H, Accession No. AK00184, Feb. 22, 2000.
Swift et al., "Tissue-specific expression of the rat pancreatic elastase I gene in transgenic mice," 38(3) Cell 639-46 (1984).
Tabas et al., "Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation," J. Biol. Chem. 268(27):20419-32 (1993).
Taira et al., Construction of a novel RNA-transcript-trimming plasmid which can be used both in vitro in place of run-off and (G)-free transcriptions and in vivo as multi-sequences transcription vectors, 19(19) Nucleic Acids Res 5125-30 (1991).
Ulmer et al., Heterologous protection against influenza by injection of DNA encoding a viral protein, 259(5102) Science 1745-9 (1993).
Ventura et al., "Activation of HIV-specific ribozyme activity by self-cleavage," 21 Nucleic Acids Res 3249-55 (1993).
Villa-Komaroff et al., "A bacterial clone synthesizing proinsulin," 75(8) Proc Nat'l Acad Sci USA 3727-31 (1978).
Visconti et al., "Expression of the neoplastic phenotype by human thyroid carcinoma cell lines requires NFkappaB p65 protein expression," Oncogene 15(16):1987-94 (1997).
Wagner et al., "Nucleotide sequence of the thymidine kinase gene of herpes simplex virus type 1," 78(3) Proc Nat'l Acad Sci USA 1441-5 (1981).
Weerasinghe et al., Resistance to human immunodeficiency virus type 1 (HIV-1) infection in human CD4+ lymphocyte-derived cell lines conferred by using retroviral vectors expressing an HIV-1 RNA-specific ribozyme, 65(10) J Virol 5531-4 (1991).
Williams et al., "Introduction of foreign genes into tissues of living mice by DNA-coated microprojectiles," 88(7) Proc Nat'l Acad Sci USA 2726-30 (1991).
Wilson et al., "Hepatocyte-directed gene transfer in vivo leads to transient improvement of hypercholesterolemia in low density lipoprotein receptor-deficient rabbits," 267(2) J Biol Chem 963-7 (1992).

(56) References Cited

OTHER PUBLICATIONS

Wu & Wu, "Receptor-mediated gene delivery and expression in vivo," 263(29) J Biol Chem 14621-4 (1988).
Wu & Wu, "Receptor-mediated in-vitro gene transformation by a soluble DNA carrier system," 262(10) J Biol Chem 4429-32 (1987).
Yamaoto et al., "Identification of a functional promoter in the long terminal repeat of Rous sarcoma virus," 22(3) Cell 787-97 (1980).
Yu et al., A hairpin ribozyme inhibits expression of diverse strains of human immunodeficiency virus type 1 90(13) Proc Nat'l Acad Sci USA 6340-4 (1993).
Zhou et al., "Synthesis of functional mRNA in mammalian cells by bacteriophage T3 RNA polymerase," 10(9) Mol Cell Biol 4529-37 (1990).
Zoller & Smith, "Oligonucleotide-directed mutagenesis: a simple method using two oligonucleotide primers and a single-stranded DNA template," 3(6) DNA 479-88 (1984).
Palu et al., "In pursuit of new developments for gene therapy of human diseases," Journal of Biotechnology, 68(1): 1-13 (1999).

* cited by examiner

Plasmid: NFIF14B
Amino Acids: 453

| Sequence | Position |
|---|---|
| MALVRALVCCLLTAWHCRSG | 20 |
| LGLPVAPAGGRNPPPAIGQF | 40 |
| WHVTDLHLDPTYHITDDHTK | 60 |
| VCASSKGANASNPGPFGDVL | 80 |
| CDSPYQLILSAFDFIKNSGQ | 100 |
| EASFMIWTGDSPPHVPVPEL | 120 |
| STDTVINVITNMTTTIQSLF | 140 |
| PNLQVFPALGNHDYWPQDQL | 160 |
| SVVTSKVYNAVANLWKPWLD | 180 |
| EEAISTLRKGGFYSQKVTTN | 200 |
| PNLRIISLNTNLYYGPNIMT | 220 |
| LNKTDPANQFEWLESTLNNS | 240 |
| QQNKEKVYIIAHVPVGYLPS | 260 |
| SQNITAMREYYNEKLIDIFQ | 280 |
| KYSDVIAGQFYGHTHRDSIM | 300 |
| VLSDKKGSPVNSLFVAPAVT | 320 |
| PVKSVLEKQTNNPGIRLFQY | 340 |
| DPRDYKLLDMLQYYLNLTEA | 360 |
| NLKGESIWKLEYILTQTYDI | 380 |
| EDLQPESLYGLAKQFTILDS | 400 |
| KQFIKYYNYFFVSYDSSVTC | 420 |
| DKTCKAFQICAIMNLDNISY | 440 |
| ADCLKQLYIKHNY | 460 |

FIG. 1

```
Plasmid:      NFIF7A
Amino Acids:  364
```

| | |
|---|---|
| MALVRALVCCLLTAWHCRSG | 20 |
| LGLPVAPAGGRNPPPAIGQF | 40 |
| WHVTDLHLDPTYHITDDHTK | 60 |
| VCASSKGANASNPGPFGDVL | 80 |
| CDSPYQLILSAFDFIKNSGQ | 100 |
| EASFMIWTGDSPPHVPVPEL | 120 |
| STDTVINVITNMTTTIQSLF | 140 |
| PNLQVFPALGNHDYWPQVYI | 160 |
| IAHVPVGYLPSSQNITAMRE | 180 |
| YYNEKLIDIFQKYSDVIAGQ | 200 |
| FYGHTHRDSIMVLSDKKGSP | 220 |
| VNSLFVAPAVTPVKSVLEKQ | 240 |
| TNNPGIRLFQYDPRDYKLLD | 260 |
| MLQYYLNLTEANLKGESIWK | 280 |
| LEYILTQTYDIEDLQPESLY | 300 |
| GLAKQFTILDSKQFIKYYNY | 320 |
| FFVSYDSSVTCDKTCKAFQI | 340 |
| CAIMNLDNISYADCLKQLYI | 360 |
| KHNY | 380 |

FIG. 2

```
1    ATGGCGCTGGTGCGCGCACTCGTCTGCTGCCTGCTGACTGCCTGGCACTG    NFIF14B
1    ATGGCGCTGGTGCGCGCACTCGTCTGCTGCCTGCTGACTGCCTGGCACTG    NFIF7A
51   CCGCTCCGGCCTCGGGCTGCCCGTGGCGCCCGCAGGCGGCAGGAATCCTC    NFIF14B
51   CCGCTCCGGCCTCGGGCTGCCCGTGGCGCCCGCAGGCGGCAGGAATCCTC    NFIF7A
101  CTCCGGCGATAGGACAGTTTTGGCATGTGACTGACTTACACTTAGACCCT    NFIF14B
101  CTCCGGCGATAGGACAGTTTTGGCATGTGACTGACTTACACTTAGACCCT    NFIF7A
151  ACTTACCACATCACAGATGACCACACAAAAGTGTGTGCTTCATCTAAAGG    NFIF14B
151  ACTTACCACATCACAGATGACCACACAAAAGTGTGTGCTTCATCTAAAGG    NFIF7A
201  TGCAAATGCCTCCAACCCTGGCCCTTTTGGAGATGTTCTGTGTGATTCTC    NFIF14B
201  TGCAAATGCCTCCAACCCTGGCCCTTTTGGAGATGTTCTGTGTGATTCTC    NFIF7A
251  CATATCAACTTATTTTGTCAGCATTTGATTTTATTAAAAATTCTGGACAA    NFIF14B
251  CATATCAACTTATTTTGTCAGCATTTGATTTTATTAAAAATTCTGGACAA    NFIF7A
301  GAAGCATCTTTCATGATATGGACAGGGGATAGCCCACCTCATGTTCCTGT    NFIF14B
301  GAAGCATCTTTCATGATATGGACAGGGGATAGCCCACCTCATGTTCCTGT    NFIF7A
351  ACCTGAACTCTCAACAGACACTGTTATAAATGTGATCACTAATATGACAA    NFIF14B
351  ACCTGAACTCTCAACAGACACTGTTATAAATGTGATCACTAATATGACAA    NFIF7A
401  CCACCATCCAGAGTCTCTTTCCAAATCTCCAGGTTTTCCCTGCGCTGGGT    NFIF14B
401  CCACCATCCAGAGTCTCTTTCCAAATCTCCAGGTTTTCCCTGCGCTGGGT    NFIF7A
451  AATCATGACTATTGGCCACAGGATCAACTGTCTGTAGTCACCAGTAAAGT    NFIF14B
451  AATCATGACTATTGGCCACAGG---------------------------    NFIF7A
501  GTACAATGCAGTAGCAAACCTCTGGAAACCATGGCTAGATGAAGAAGCTA    NFIF14B
473  --------------------------------------------------    NFIF7A
551  TTAGTACTTTAAGGAAAGGTGGTTTTTATTCACAGAAAGTTACAACTAAT    NFIF14B
473  --------------------------------------------------    NFIF7A
601  CCAAACCTTAGGATCATCAGTCTAAACACAAACTTGTACTACGGCCCAAA    NFIF14B
473  --------------------------------------------------    NFIF7A
651  TATAATGACACTGAACAAGACTGACCCAGCCAACCAGTTTGAATGGCTAG    NFIF14B
473  --------------------------------------------------    NFIF7A
701  AAAGTACATTGAACAACTCTCAGCAGAATAAGGAGAAGGTGTATATCATA    NFIF14B
473  ----------------------------------------TGTATATCATA    NFIF7A
751  GCACATGTTCCAGTGGGGTATCTGCCATCTTCACAGAACATCACAGCAAT    NFIF14B
484  GCACATGTTCCAGTGGGGTATCTGCCATCTTCACAGAACATCACAGCAAT    NFIF7A
801  GAGAGAATACTATAATGAGAAATTGATAGATATTTTTCAAAAATACAGTG    NFIF14B
534  GAGAGAATACTATAATGAGAAATTGATAGATATTTTTCAAAAGTACAGTG    NFIF7A
851  ATGTCATTGCAGGACAATTTTATGGACACACTCACAGAGACAGCATTATG    NFIF14B
584  ATGTCATTGCAGGACAATTTTATGGACACACTCACAGAGACAGCATTATG    NFIF7A
901  GTTCTTTCAGATAAAAAAGGAAGTCCAGTAAATTCTTTGTTTGTGGCTCC    NFIF14B
634  GTTCTTTCAGATAAAAAAGGAAGTCCAGTAAATTCTTTGTTTGTGGCTCC    NFIF7A
```

FIG. 3

```
951   TGCTGTTACACCAGTGAAGAGTGTTTTAGAAAAACAGACCAACAATCCTG    NFIF14B
684   TGCTGTTACACCAGTGAAGAGTGTTTTAGAAAAACAGACCAACAATCCTG    NFIF7A
1001  GTATCAGACTGTTTCAGTATGATCCTCGTGATTATAAATTATTGGATATG    NFIF14B
734   GTATCAGACTGTTTCAGTATGATCCTCGTGATTATAAATTATTGGATATG    NFIF7A
1051  TTGCAGTATTACTTGAATCTGACAGAGGCGAATCTAAAGGGAGAGTCCAT    NFIF14B
784   TTGCAGTATTACTTGAATCTGACAGAGGCGAATCTAAAGGGAGAGTCCAT    NFIF7A
1101  CTGGAAGCTGGAGTATATCCTGACCCAGACCTACGACATTGAAGATTTGC    NFIF14B
834   CTGGAAGCTGGAGTATATCCTGACCCAGACCTACGACATTGAAGATTTGC    NFIF7A
1151  AGCCGGAAAGTTTATATGGATTAGCTAAACAATTTACAATCCTAGACAGT    NFIF14B
884   AGCCGGAAAGTTTATATGGATTAGCTAAACAATTTACAATCCTAGACAGT    NFIF7A
1201  AAGCAGTTTATAAAATACTACAATTACTTCTTTGTGAGTTATGACAGCAG    NFIF14B
934   AAGCAGTTTATAAAATACTACAATTACTTCTTTGTGAGTTATGACAGCAG    NFIF7A
1251  TGTAACATGTGATAAGACATGTAAGGCCTTTCAGATTTGTGCAATTATGA    NFIF14B
984   TGTAACATGTGATAAGACATGTAAGGCCTTTCAGATTTGTGCAATTATGA    NFIF7A
1301  ATCTTGATAATATTTCCTATGCAGATTGCCTCAAACAGCTTTATATAAAG    NFIF14B
1034  ATCTTGATAATATTTCCTATGCAGATTGCCTCAAACAGCTTTATATAAAG    NFIF7A
1351  CACAATTACTAG                                          NFIF14B
1084  CACAATTACTAG                                          NFIF7A
```

FIG. 3 (CONT'D)

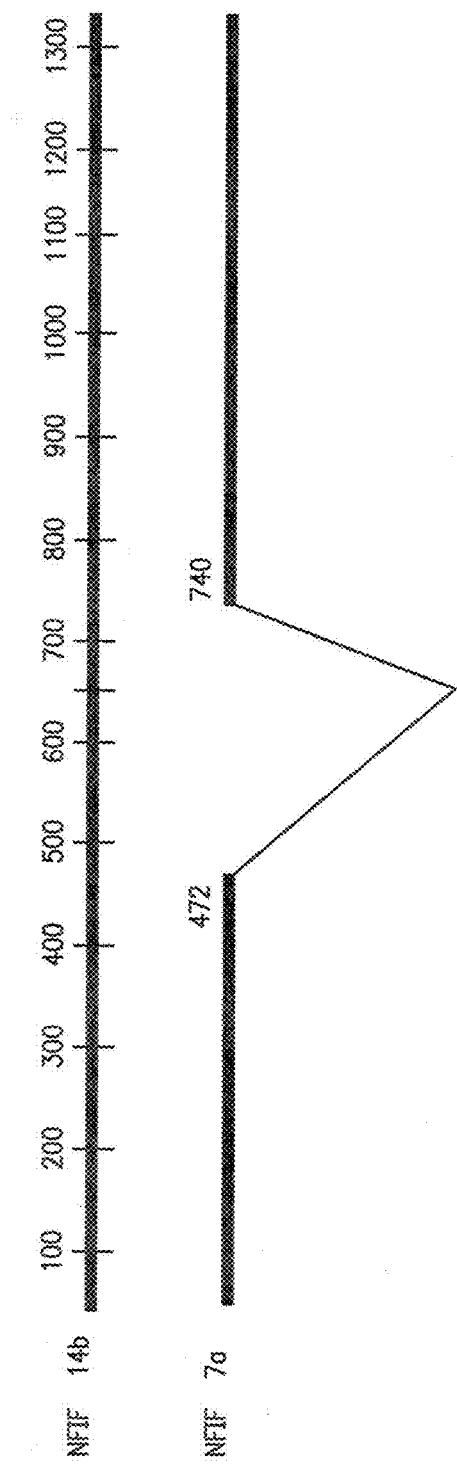

SKGANASNPGPFGDV

FIG. 7

NUCLEAR FACTOR κB INDUCING FACTOR

FIELD OF THE INVENTION

Nuclear factor κB (NFκB) comprises a family of eukaryotic transcription factors involved in regulation of genes involved in immune responses and other cellular functions. In some instances, NFκB activation leads to an inflammatory response which ultimately results in a disease state. Accordingly, it would be desirable to develop means for controlling induction of NFκB. The present invention provides polypeptides which are involved in the induction of NFκB and which may be used to enhance NFκB expression or activation or to identify and prepare inhibitors of NFκB expression or activation.

REPORTED DEVELOPMENTS

Nuclear factor κB (NFκB) comprises a family of transcription factors found in almost all eukaryotic cells. NFκB plays a role in the regulation of genes involved in tissue inflammation, cellular proliferation, and cellular differentiation.

A number of studies have examined the relationship between disease states and expression of the subunit proteins which comprise NFκB or activation of NFκB already present in a cell. Li et al. studied the regulation of NFκB by the HTLV-1 Tax protein demonstrating that the ability of Tax to activate the NFκB pathway plays an essential role in HTLV-1-induced cellular transformation (Li et al., *Gene Expr.*, 7, 4-6, 233-245 (1999)). Lentsch and Ward studied the activation and regulation of NFκB during acute inflammation and described the relationship between NFκB and the inhibiting proteins of the IKappaB family (Lentsch et al., *Clin. Chem. Lab. Med.*, 37, 3, 205-208 (1999)). Visconti et al. investigated the role of NFκB in thyroid carcinogenesis by analyzing thyroid carcinoma cell lines. Their studies indicated that activation of the NFκB complex by overexpression of the p65 protein played a critical role in the process of thyroid cell transformation (Visconti et al., *Oncogene*, 15, 16, 1987-1994 (1997)). Mukhopadhyay et al. investigated the expression of the p50 subunit of NFκB transcription factor complex in non-small cell lung carcinoma tissues demonstrating that 81% of fresh non-small cell lung cancer tissues express from two to twenty-fold higher levels of the p50 subunit than normal lung tissue (Mukhopadhyay et al., *Oncogene*, 11, 5, 999-1003 (1995)). Khaled et al. targeted p50 gene expression with specific antisense 3' phosphorothioate modified antisense oligodeoxynucleotides and were able to reduce NFκB expression. Their results demonstrated p50 antisense molecules could reduce NFκB expression and could down-regulate the immune response providing possible treatment for autoimmune disorders (Khaled et al., *Clin. Immunol. Immunopathol.*, 83, 3, 254-263 (1997)).

SUMMARY OF THE INVENTION

In accordance with the present invention, there are provided nucleic acid sequences encoding nuclear factor κB inducing factor (NFIF) 14b and 7a. Included also are cDNAs encoding NFIF-14b and NFIF-7a and isolated and purified NFIF-14b and NFIF-7a polypeptides which induce NFκB. The present invention includes also methods of inducing NFκB comprising introducing into the body of a patient a composition that activates NFκB induction, including for example, expression vectors that express NFIF-14b and NFIF-7a polypeptides. Examples of preferred expression vectors are retroviral vectors, adenoviral vectors, adeno-associated viral vectors, herpes, herpesviral vectors and naked DNA vectors. The present invention also provides methods wherein the composition of the present invention comprise an NFIF-14b or NFIF-7a polypeptide and a pharmaceutically acceptable carrier.

Another aspect of the present invention are compositions for lowering the expression of the NFIF gene comprising an antisense nucleic acid. Still another aspect of the present invention is a composition for lowering the activity of an NFIF polypeptide comprising a neutralizing antibody that binds to an NFIF polypeptide and lowers its activity.

Yet another embodiment of the present invention is a composition for lowering the expression of NFIF in a patient comprising a ribozyme that cuts RNA encoding an NFIF polypeptide.

The present invention provides methods for evaluating whether a test compound is effective in inhibiting the activity of NFIF-14b polypeptides comprising (A) comparing the level of NFκB-regulated gene expression in a first sample comprising: (1) NFIF-14b; (2) the NFκB-regulated reporter gene; and (3) the test compound with the level of gene expression in a second sample comprising (4) NFIF-14b; and (5) the NFκB-regulated reporter gene; and (B) determining whether the expression of the reporter gene is lower in the first sample relative to the second sample.

Still another aspect of the present invention provides methods for evaluating whether a test compound is effective in inhibiting the activity of NFIF-7a polypeptides comprising (A) comparing the level of NFκB-regulated gene expression in a first sample comprising: (1) NFIF-7a; (2) the NFκB-regulated reporter gene; and (3) the test compound with the level of gene expression in a second sample comprising (4) NFIF-7a; and (5) the NFκB-regulated reporter gene; and (B) determining whether the expression of the reporter gene is lower in the first sample relative to the second sample.

Yet another aspect of the present invention provides a method for identifying whether a test compound can enhance the activity of NFIF-14b based on the expression of an NFκB regulator reporter gene comprising (A) comparing the level of NFκB-regulated gene expression in a first sample comprising (1) NFIF-14b; (2) the NFκB-regulated reporter gene; and (3) the test compound with the level of gene expression in a second sample comprising: (4) NFIF-14b; and (5) the NFκB-regulated reporter gene; and (B) determining whether the expression of the reporter gene is higher in the first sample relative to the second sample.

Another aspect of the present invention provides a method for identifying whether a test compound can enhance the activity of NFIF-7a based on the expression of an NFκB regulator reporter gene comprising (A) comparing the level of NFκB-regulated gene expression in a first sample comprising (1) NFIF-7a; (2) the NFκB-regulated reporter gene; and (3) the test compound with the level of gene expression in a second sample comprising: (4) NFIF-7a; and (5) the NFκB-regulated reporter gene; and (B) determining whether the expression of the reporter gene is higher in said first sample relative to the second sample.

In yet another aspect of the present invention, methods are provided for inhibiting expression of NFκB-dependent genes comprising administering to a patient a composition that inhibits the activity of NFIF-14b or NFIF-7a.

Still yet another aspect of the present invention is a method of inhibiting inflammation comprising administration of a composition that inhibits the activity of NFIF-14b or NFIF-7a.

Another aspect of the present invention relates to the use of an NFIF polypeptide for the manufacture of a medicament intended for the treatment and/or prevention of an NFκB-regulated inflammatory response. Still yet another aspect of the present invention relates to the use of a nucleic acid encoding an NFIF polypeptide, for the manufacture of a medicament intended for the treatment and/or prevention of an NFκB-regulated inflammatory response.

Another aspect of the present invention relates to the use of a recombinant vector comprising a nucleic acid encoding an NFIF polypeptide, for the manufacture of a medicament intended for the treatment and/or prevention of an NFκB-regulated inflammatory response. Yet another aspect of the present invention relates to the use of a defective recombinant viral vector for the manufacture of a medicament intended for the treatment and/or prevention of an NFκB-regulated response.

Another aspect of the present invention relates to the use of cells genetically modified ex vivo with a recombinant virus or production of cells containing such recombinant viruses which are implanted in the body, facilitating prolonged and effective expression in vivo of an NFIF polypeptide according to the invention.

Two sequences demonstrating similarities to the polypeptides of the present invention are available in the GenBank nucleic acid sequence library. The first sequence, having Accession Number Y08135 encodes a peptide identified as full-length mouse acid sphingomyelinase-like phosphodiesterase 3a. The second sequence, having Accession Number Y08136 encoded a partial human clone (863 bp of which 536 were coding) for a protein sequence identified as human acid sphingomyelinase-like phosphodiesterase 3a. Both sequences were submitted on Sep. 17, 1996 by K. Hofmann. Although both of these sequences were identified as encoding acid sphingomyelinase-like phosphodiesterases, there has not been confirmation of this type of enzymatic activity. These sequences may have been identified as acid sphingomyelinase-like phosphodiesterases due to similarities between the 3' sequences of these proteins and the 3' sequences of members of the sphingomyelinase family.

BRIEF DESCRIPTION OF THE DRAWINGS

FIG. 1 is the amino acid sequence for NFIF-14b.
FIG. 2 is the amino acid sequence for NFIF-7a.
FIG. 3 is the cDNA sequence for NFIF-14b and NFIF-7a aligned for comparison.
FIG. 4 is a diagrammatic representation of NFIF-14b and NFIF-7a.
FIG. 7 is the amino acid sequence of a 15-residue sequence used to prepare antibodies directed against NFIF.

DETAILED DESCRIPTION OF THE INVENTION

Figure 5:
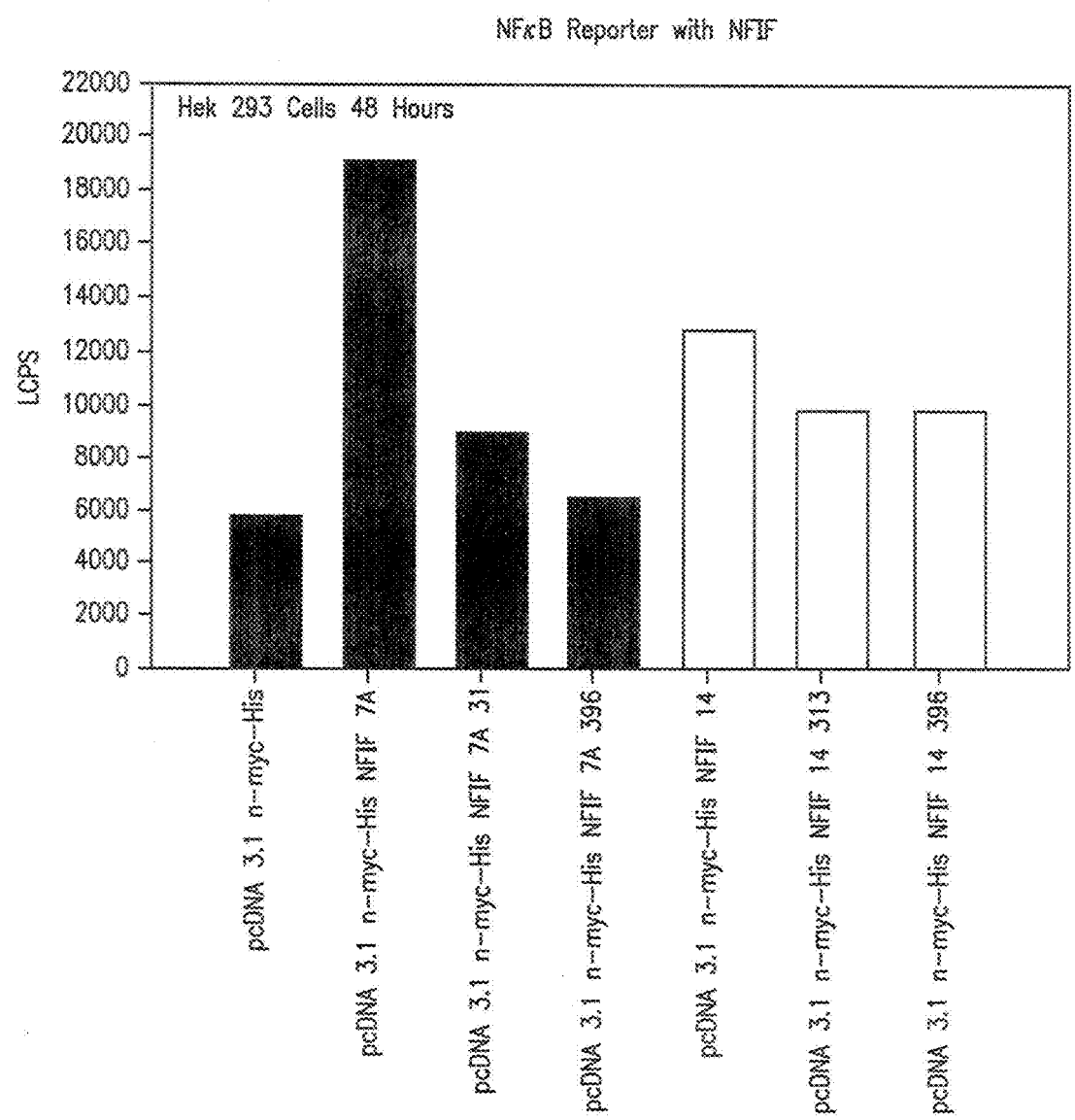
FIG. 5 is a bar graph representing luminometer counts per second observed in HeK 293 cells at 48 hours.

The present invention provides polypeptides which are capable of inducing NFκB as well as compounds and compositions that are capable of inhibiting induction of NFκB.

The present invention is based in part on the discovery of NFκB-inducing factor (NFIF) proteins. Two functional variants of the NFIF protein have been identified. One variant, NFIF-14b, comprises full-length NFIF. The second variant, NFIF-7a, is believed to be a splice variant of NFIF-14b. Both NFIF-14b and NFIF-7a have the ability to induce NFκB.

NFκB comprises a family of eukaryotic transcription factors which regulate genes involved in immune responses and other cellular activities. In certain situations, it may be desirable to induce NFκB in order to initiate or increase the extent of an immune response. In other situations, it may be desirable to reduce or prevent NFκB induction in order to reduce or prevent an NFκB-regulated immune response. For example, it has been discovered that NFIF is associated with a variety of pathologies associated with NFκB-regulated immune responses, including atherosclerosis. By inhibiting the expression of the NFIF gene, or by otherwise interfering with the activity of the NFIF protein, it is possible to inhibit NFκB induction, thereby inhibiting or preventing NFκB-regulated inflammatory responses that result in atherosclerosis and other diseases.

Discovery of the gene encoding NFIF and the ability to prepare NFIF proteins facilitates identification and preparation of compounds and compositions which are capable of inhibiting the activity of NFIF proteins and consequently inhibiting NFκB induction.

The description which follows begins with a Definitions section, followed by background information relating to NFκB. This is followed by a discussion of the NFIF polypeptides of the present invention, as well as information on isolation of DNA encoding such polypeptides and methods for preparing variants of the polypeptides. Expression vectors capable of expressing the encoding NFIF polypeptide DNAs are then discussed, including information on appropriate promoters for the expression systems, methods for introducing the expression vectors into appropriate host cells and viral vector systems. Following this discussion of NFIF polypeptides and their variants, there is a discussion of therapeutic uses for NFIF polypeptides. This discussion is followed by a description of compositions useful in the practice of the present invention. This is followed by a discussion which outlines the various therapeutic compositions and compounds, including polypeptides based on NFIF, antisense nucleic acids, ribozymes and antibodies. Finally, the methods of the present invention which use the described compounds and compositions are described.

DEFINITIONS

The term "NFIF" is used to designate "nuclear factor κB-inducing factor".

The terms "inducing" or "induction" when used in describing the activity of NFIF include within their scope the ability to cause expression of the subunit proteins which comprise NFκB either directly or indirectly as well as the ability to activate NFκB that is already present in a cell. This activation may be direct or indirect and results in NFκB functioning as a transcription factor.

For the purposes of the present description, the expression "nucleotide sequence" may be used to designate either a polynucleotide or a nucleic acid. The expression "nucleotide sequence" covers the genetic material itself and is therefore not restricted to the information relating to its sequence.

The terms "nucleic acid", "polynucleotide", "oligonucleotide" or "nucleotide sequence" cover RNA, DNA, gDNA or cDNA sequences or alternatively RNA/DNA hybrid sequences of more than one nucleotide, either in the single-stranded form or in the duplex, double-stranded form.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence or coding sequence.

The term "nucleotide" designates both the natural nucleotides (A, T, G, C) as well as the modified nucleotides that comprise at least one modification such as (1) an analog of a purine, (2) an analog of a pyrimidine, or (3) an analogous sugar, examples of such modified nucleotides being described, for example, in the PCT application No. WO 95/04064.

For the purposes of the present invention, a first polynucleotide is considered as being "complementary" to a second polynucleotide when each base of the first nucleotide is paired with the complementary base of the second polynucleotide whose orientation is reversed. The complementary bases are A and T (or A and U), or C and G.

"Heterologous" DNA refers to DNA not naturally located in the cell, or in a chromosomal site of the cell. Preferably, the heterologous DNA includes a gene foreign to the cell.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell, 50:667 (1987)). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and more preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., Molecular cloning: A Laboratory Manual, Cold Spring Harbor Press, Cold Spring, N.Y. (1982); Glover et al., *DNA Cloning: A Practical Approach, Volumes I and II Oligonucleotide Synthesis*, MRL Press, Ltd., Oxford, U.K. (1985); Hames and Higgins, Hames B D and Higgins S J, 1985. *Nucleic acid hybridization: a practical approach*, Hames and Higgins Ed., IRL Press, Oxford (1985)).

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The "percentage identity" between two nucleotide or amino acid sequences, for the purposes of the present invention, may be determined by comparing two sequences aligned optimally, through a window for comparison.

The portion of the nucleotide or polypeptide sequence in the window for comparison may thus comprise additions or deletions (for example "gaps") relative to the reference sequence (which does not comprise these additions or these deletions) so as to obtain an optimum alignment of the two sequences.

The percentage is calculated by determining the number of positions at which an identical nucleic base or an identical amino acid residue is observed for the two sequences (nucleic or peptide) compared, and then by dividing the number of positions at which there is identity between the two bases or amino acid residues by the total number of positions in the window for comparison, and then multiplying the result by 100 in order to obtain the percentage sequence identity.

The optimum sequence alignment for the comparison may be achieved using a computer with the aid of known algorithms contained in the package from the company WISCONSIN GENETICS SOFTWARE PACKAGE, GENETICS COMPUTER GROUP (GCG), 575 Science Doctor, Madison, Wis.

By way of illustration, it will be possible to produce the percentage sequence identity with the aid of the BLAST software (versions BLAST 1.4.9 of March 1996, BLAST 2.0.4 of February 1998 and BLAST 2.0.6 of September 1998), using exclusively the default parameters (Altschul et al, *J. Mol. Biol.*, 215:403-410 (1990); Altschul et al, *Nucleic Acids Res.*, 25:3389-3402 (1997)). Blast searches for sequences similar/homologous to a reference "request" sequence, with the aid of the Altschul et al. algorithm. The request sequence and the databases used may be of the peptide or nucleic types, any combination being possible.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

"Variant" of a nucleic acid according to the invention will be understood to mean a nucleic acid that differs by one or more bases relative to the reference polynucleotide. A variant nucleic acid may be of natural origin, such as an allelic variant that exists naturally, or it may also be a non-natural variant obtained, for example, by mutagenic techniques.

In general, the differences between the reference (generally, wild-type) nucleic acid and the variant nucleic acid are small such that the nucleotide sequences of the reference nucleic acid and of the variant nucleic acid are very similar and, in many regions, identical. The nucleotide modifications present in a variant nucleic acid may be silent, which means that they do not alter the amino acid sequences encoded by said variant nucleic acid.

However, the changes in nucleotides in a variant nucleic acid may also result in substitutions, additions or deletions in the polypeptide encoded by the variant nucleic acid in relation to the polypeptides encoded by the reference nucleic acid. In addition, nucleotide modifications in the coding regions may produce conservative or non-conservative substitutions in the amino acid sequence of the polypeptide.

Preferably, the variant nucleic acids according to the invention encode polypeptides that substantially conserve the same function or biological activity as the polypeptide of the reference nucleic acid or alternatively the capacity to be recognized by antibodies directed against the polypeptides encoded by the initial reference nucleic acid.

Some variant nucleic acids will thus encode mutated forms of the polypeptides whose systematic study will make it possible to deduce structure-activity relationships of the proteins in question. Knowledge of these variants in relation to the disease studied is essential since it makes it possible to understand the molecular cause of the pathology.

"Fragment" will be understood to mean a nucleotide sequence of reduced length relative to the reference nucleic acid and comprising, over the common portion, a nucleotide sequence identical to the reference nucleic acid. Such a nucleic acid "fragment" according to the invention may be, where appropriate, included in a larger polynucleotide of which it is a constituent. Such fragments comprise, or alternatively consist of, oligonucleotides ranging in length from 8, 10, 12, 15, 18, 20 to 25, 30, 40, 50, 70, 80, 100, 200, 500, 1000 or 1500 consecutive nucleotides of a nucleic acid according to the invention.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, or in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular cloning: a laboratory manual*. 2ed. Cold Spring Harbor Laboratory, Cold spring Harbor, N.Y. (1989)). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"High stringency hybridization conditions" for the purposes of the present invention will be understood to mean the following conditions:

1—Membrane Competition and Prehybridization:
Mix: 40 µl salmon sperm DNA (10 mg/ml)
40 µl human placental DNA (10 mg/ml)
Denature for 5 minutes at 96° C., then immerse the mixture in ice.
Remove the 2×SSC and pour 4 ml of formamide mix in the hybridization tube containing the membranes.
Add the mixture of the two denatured DNAs.
Incubation at 42° C. for 5 to 6 hours, with rotation.
2—Labeled Probe Competition:
Add to the labeled and purified probe 10 to 50 µl Cot I DNA, depending on the quantity of repeats.
Denature for 7 to 10 minutes at 95° C.
Incubate at 65° C. for 2 to 5 hours.
3—Hybridization:
Remove the prehybridization mix.
Mix 40 µl salmon sperm DNA+40 µl human placental DNA; denature for 5 min at 96° C., then immerse in ice.
Add to the hybridization tube 4 ml of formamide mix, the mixture of the two DNAs and the denatured labeled probe/Cot I DNA.
Incubate 15 to 20 hours at 42° C., with rotation.
4—Washes and Exposure:
One wash at room temperature in 2×SSC, to rinse.
Twice 5 minutes at room temperature 2×SSC and 0.1% SDS at 65° C.
Twice 15 minutes at 65° C. 1×SSC and 0.1% SDS at 65° C.
Envelope the membranes in clear plastic wrap and expose.

The hybridization conditions described above are adapted to hybridization, under high stringency conditions, of a molecule of nucleic acid of varying length from 20 nucleotides to several hundreds of nucleotides. It goes without saying that the hybridization conditions described above may be adjusted as a function of the length of the nucleic acid whose hybridization is sought or of the type of labeling chosen, according to techniques known to one skilled in the art. Suitable hybridization conditions may, for example, be adjusted according to the teaching contained in the manual by Hames and Higgins (1985), supra or in the manual by F. Ausubel et al., Current Protocols in Molecular Biology, Green Publishing Associates and Wiley Interscience, N.Y. (1989).

Nuclear Factor κB

Nuclear factor κB (NFκB) comprises a family of eukaryotic transcription factors. The NFκB transcription factors were first identified as factors which bound the enhancer elements in the κ light chain gene in murine B lymphocytes. Subsequent studies demonstrated NFκB is found in almost all cells and regulates genes involved in tissue inflammation, cellular proliferation and cellular differentiation.

NFκB comprises at least five subunits: p50, p52, p65 (RelA), c-Rel, and RelB which can form homo- and heterodimers in various combinations. Active forms of NFκB are usually heterodimers comprised of p65 (RelA) and p50.

In most cells, NFκB exists as an inactive heterodimer which is sequestered in the cytosol due to association with an inhibitory protein I-κB. In response to stimuli such as inflammatory stimuli, the I-κB protein is phosphorylated and degraded, resulting in disassociation of the I-κB-NFκB complex and translocation of NFκB into the nucleus. Once in the nucleus, NFκB recognizes specific enhancer sites containing the NFκB DNA binding motif and interacts with basal transcription factors to initiate RNA polymerase II mediated transcription in conjunction with the TATA box binding protein. As mentioned above, this results in the transcription of a wide variety of genes, particularly genes involved in immune and inflammatory responses.

As mentioned above, the present invention is based in part on the discovery of nuclear factor κB-inducing factor (NFIF) proteins. These proteins are involved in induction of NFκB. Discovery of these NFIF proteins provides different approaches to treating conditions that involve NFκB-regulated inflammatory responses. NFκB-regulated inflammatory responses are associated with a variety of disease states which include, but are not limited to, rheumatoid arthritis, atherosclerosis, autoimmune diseases, viral diseases, NSAID-induced gastropathy, neurodegenerative diseases, scrapie, sepsis, apoptosis, Crohn's disease, renal disease, restenosis, brain injury/inflammation, Alzheimer's disease, asthma, and improperly regulated expression of pleiotropic cytokines. In situations where it is desirable to increase induction of NFκB for the purpose of resulting in an increased immune response, the NFIF proteins of the present invention can be introduced to or expressed in a patient to induce NFκB. If, on the other hand, it is desirable to inhibit induction of NFκB in order to inhibit or prevent an immune response, the provision according to the present invention of the genetic sequences encoding the NFIF proteins and of how to prepare these proteins can be used to identify compounds and compositions which inhibit or prevent expression of the NFIF proteins or which interact with NFIF proteins to inhibit or prevent their activity.

Nuclear Factor κB Inducing Factor (NFIF) Proteins

The polypeptides and proteins of the present invention include recombinant polypeptides, natural polypeptides, or synthetic polypeptides, and can be of human, rabbit, or other animal origin.

The polypeptides can be isolated from natural sources, such as placental extracts, human plasma, or conditioned media from cultured cells using purification procedures known to one of skill in the art.

Alternatively, the polypeptides of the present invention can be prepared utilizing recombinant DNA technology which comprises combining a nucleic acid encoding the polypeptide thereof in a suitable vector, inserting the resulting vector into a suitable host cell, recovering the polypeptide produced by the resulting host cell, and purifying the polypeptide recovered.

The polypeptides are characterized by a reproducible single molecular weight and/or multiple set of molecular weights, chromatographic properties and elution profiles, amino acid composition and sequence, and biological activity.

Isolation of Nucleotide Sequences Encoding NFIF Polypeptides

The NFIF-14b and NFIF-7a embodiments of the present invention can be prepared by a variety of suitable methods known to those of skill in the art. Teachings on general molecular biology, microbiology, and recombinant DNA techniques within the skill of the art are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); F. M. Ausubel et al. (eds.), *Current Protocols in Molecular Biology*, John Wiley & Sons, Inc. (1994).

The cDNA sequence for NFIF-14b and NFIF-7a are presented in FIG. 3. NFIF-7a is a splice variant of NFIF-14b. The term "splice variant" refers to a polypeptide encoded by an mRNA produced by alternative processing of the full length mRNA encoded by a gene or genes resulting in an mRNA that contains one or more deletions relative to the full length mRNA for the genes. As shown in FIG. 4, relative to NIFI-14b, NFIF-7a has an internal deletion of base pairs 473 to 739. Given the information in the description herein on the DNA sequence of NFIF-14b and NFIF-7a and the known methods in the art for obtaining cDNA, nucleotide sequences encoding NFIF-14b and NFIF-7a can be cloned readily and inserted into an appropriate vector for expression of these proteins in vitro or in vivo. For a description of methods relating to cloning cDNA and expression vectors, see Sambrook et al., 1989, supra. A "cloning vector" is a replicon, for example, a plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. A cloning vector may be capable of replication in one cell type and expression in another ("shuttle vector"). In preferred embodiments of the present invention, the cloning vector is capable of expression in a host cell and the "expression vector" is able to express NFIF at sufficient levels to effect an NFκB regulated pathway in the cell.

A gene encoding NFIF-14b and NFIF-7a, whether genomic DNA or cDNA, can be isolated from a human genomic library or cDNA library. A DNA "coding sequence" is a double-stranded DNA sequence which is transcribed and translated into a polypeptide in a cell in vitro or in vivo when placed under the control of appropriate regulatory sequences. The DNA coding sequences and the appropriate regulatory sequences are preferably provided in an expression vector. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence. Methods for obtaining a gene given the DNA sequence information presented herein are well known in the art. The DNA may be obtained by standard procedures known in the art from cloned DNA (e.g., a DNA "library"). It is obtained preferably from a cDNA library prepared from tissues with high level expression of the protein. The DNA may also be obtained by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II) or by chemical synthesis. Clones derived from genomic DNA may contain regulatory and intron DNA regions in addition to coding regions.

Methods for obtaining cDNA are well known in the art. Briefly, these methods include isolating a mixture of messenger RNA (mRNAs) from eukaryotic cells and employing a series of enzymatic reactions to synthesize double-stranded DNA copies (cDNAs) complementary to the isolated mRNAs. "Polymerase chain reaction" (PCR) refers to in vitro methods for amplifying specific DNA sequences using techniques well known in the art.

Regardless of the method used to obtain the desired cDNA, the double-stranded cDNA mixture is inserted into cloning vehicles by any one of many known techniques, depending at least in part on the particular vehicle used. Various insertion methods are discussed in Sambrook et al., 1989, supra and are well known in the art. A "cassette" refers to a segment of DNA that can be inserted into a vector at one or more specific restriction sites. The segment of DNA encodes a polypeptide of interest and the cassette and restriction sites are designed to ensure insertion of the cassette in the proper reading frame for transcription and translation.

Once the DNA segments are inserted into a cloning vehicle, the cloning vehicle is used to transform a suitable host. A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell. These cloning vehicles usually impart an antibiotic resistance trait on the host. Such hosts are generally prokaryotic cells and only a few of the host cells contain the desired cDNA. The transfected host cells constitute a gene "library", providing a representative sample of the mRNAs present in the cell from which the mRNAs were isolated.

Given the sequence information on NFIF-14b and NFIF-7a provided herein, an appropriate oligonucleotide may be prepared, preferably synthesized as discussed above, and used to identify clones containing NFIF sequences. The oligonucleotide preferably includes at least about 18 nucleotides and is hybridizable to a genomic DNA molecule, a cDNA molecule, or an mRNA molecule encoding NFIF. Oligonucleotides can be labeled, e.g., with $^{32}$P-nucleotides or nucleotides to which a label, such as biotin, has been covalently conjugated.

In one embodiment, a labeled oligonucleotide can be used as a probe to detect the presence of a nucleic acid encoding NFIF. In another embodiment, oligonucleotides (one or both of which may be labeled) can be used as PCR primers, either for cloning full length or a fragment of NFIF, or to detect the presence of nucleic acids encoding NFIF. In a further embodiment, an oligonucleotide can form a triple helix with an NFIF DNA molecule.

Generally, oligonucleotides are prepared synthetically, preferably on a nucleic acid synthesizer. Accordingly, oligonucleotides can be prepared with non-naturally occurring phosphoester analog bonds, such as thioester bonds, etc. To identify clones containing the NFIF sequences, individual transformed or transfected cells are grown as colonies on a nitrocellulose filter paper. The colonies are lysed and the DNA is bound tightly to the filter paper by heating. The filter paper is then incubated with a labeled oligonucleotide probe which is complementary to NFIF. DNA fragments with substantial homology to NFIF will hybridize to the probe.

As discussed above, the conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art.

The probe hybridizes with the cDNA for which it is complementary. It can be identified by autoradiography or by chemical reactions that identify the presence of the probe. The corresponding clones are characterized in order to identify one or a combination of clones which contain all of the structural information for the desired protein. The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA. Transcriptional and translational control sequences are DNA regulatory sequences, such as, for example, promoters, enhancers, and terminators that provide for the expression of a coding sequence in a host cell. In eukaryotic cells, polyadenylation signals are control sequences. A coding sequence is "under the control" of transcriptional and translational control sequences in a cell when RNA polymerase transcribes the coding sequence into mRNA, which is then spliced (if the coding sequence contains introns) and translated into the protein encoded by the coding sequence.

Further selection can be carried out on the basis of the properties of the gene. For example, the presence of the desired gene in a clone may be detected by assays based on the physical, chemical, or immunological properties of its expressed protein product. For example, cDNA clones, or DNA clones can be selected which produce a protein that has similar or identical properties to those of NFIF with regard to electrophoretic migration, isoelectric focusing, non-equilibrium pH gel electrophoresis, proteolytic digestion, or antigenicity.

Preparation of Variants of NFIF Polypeptides

The present invention includes within its scope allelic variants, substitution, addition and deletion mutant variants, analogs, and derivatives of NFIF and homologs from other species that have the same or homologous functional activity as NFIF. In preferred embodiments, genes having deletions or substitutions that increase the ability to induce NFκB are utilized in the practice of the invention. Preparation or isolation of NFIF variants are within the scope of the present invention. Accordingly, the scope of the present invention includes NFIF variants which are functionally active, i.e., capable of exhibiting one or more functional activities associated with NFIF.

NFIF variants can be made by altering encoding nucleic acid sequences by substitutions, additions or deletions that provide for functionally equivalent molecules. Preferably, NFIF embodiments are made that have enhanced or increased functional activity relative to NFIF-14b or NFIF-7a.

Due to the degeneracy of nucleotide coding sequences, other DNA sequences which encode substantially the same amino acid sequence as NFIF, including an amino acid sequence that contains a single amino acid variant, can be used in the practice of the present invention. These include, but are not limited to, allelic genes, homologous genes from other species, and nucleotide sequences comprising all or portions of NFIF which are altered by the substitution of different codons that encode the same amino acid residue within the sequence, thus producing a silent change. Likewise, the NFIF variants of the invention include, but are not limited to, those containing, as a primary amino acid sequence, all or part of the amino acid sequence of a NFIF protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence can be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particularly preferable property. For example, a Cys may be introduced as a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding NFIF variants of the invention can be produced by various methods known in the art. The manipulations which result in their production can occur at the gene or protein level. For example, the cloned NFIF gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a NFIF embodiment, care should be taken to ensure that the modified gene remains within the same translational reading frame as the NFIF gene, uninterrupted by translational stop signals, in the gene region where the desired activity is encoded.

Additionally, the NFIF-encoding nucleic acid sequence can be mutated in vitro or in vivo to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated NFIF gene product. Any technique for mutagenesis known in the art can be used, for example, in vitro site-directed mutagenesis (Hutchinson, C., et al., 1978, *J. Biol. Chem.* 253:6551; Zoller and Smith, 1984, DNA 3:479-488; Oliphant et al., 1986, *Gene* 44:177; Hutchinson et al., 1986, *Proc. Natl. Acad. Sci. U.S.A.* 83:710), and use of "TAB" linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

Polypeptides Based on NFIF

A therapeutically useful variant of NFIF may be identified by a variety of methods, including in vitro assays that can be used to identify the level of expression of an NFκB regulated gene or a gene whose expression is regulated by NFκB regulatory elements in the presence of the NFIF variant. One method for identifying polypeptides which are able to enhance (or inhibit) NFκB induction is to use a reporter gene system. These systems utilize reporter gene expression vectors which include a cloning site into which a given promoter may be cloned upstream of a "reporter gene" which can be easily detected and quantified. One of skill in the art could readily identify and subclone the promoter for NFκB as well as other control sequences into a commercially available reporter gene expression vector. The expression vector is transferred into host cells and the cells are exposed to an NFIF variant (or a putative inhibitor or enhancer molecule) to determine the effect on expression of the reporter gene product. In particular, the cells are assayed for the presence of the reporter gene product directly by measuring the amount of reporter mRNA, the reporter protein itself or the enzymatic activity of the reporter protein. Ideally, the reporter gene is not endogenously expressed in the cell type of interest and lends itself to sensitive, quantitative and rapid assays. A variety of reporter assay constructs are commercially available and several reporter genes and assays have been developed and can be readily prepared by those of skill in the art. The most popular systems for monitoring genetic activity in eukaryotic cells include chloramphenicol acetyltransferase (CAT), β-galactosidase, firefly luciferase, growth hormone (GH), β-glucurorudase (GUS), alkaline phosphatase (AP), green fluorescent protein (GFP) and *Renilla luciferase*. Reporter assay constructs can be purchased from a variety of sources including Promega and Invitrogen.

As mentioned above, reporter gene activity can be detected by assaying for the reporter mRNA or the reporter protein. The reporter mRNA can be detected by northern blot analysis, ribonuclease protection assays or RT-PCR. While these assays are more direct than measuring protein expression, many assays have been developed to measure the presence of the reporter protein rather than the mRNA present in a cell. Reporter proteins can be assayed by spectrophotometry or by detecting enzymatic activity. Reporter protein levels may also be measured with antibody-based assays. In general, the enzymatic assays are very sensitive and are a preferred method of monitoring reporter gene expression. A preferred commercially available NFκB reporter gene construct is the pNFκB-Luc (luciferase) reporter gene vector available from Stratagene. An example of how to utilize this reporter system to quantify NFIF protein activity is provided in Example 4.

Experiments of the type discussed hereinabove can be utilized to determine how well a given disease state can be treated using the compositions of the present invention.

The discussion which follows relates to the manipulation and expression of DNA encoding the polypeptides of the present invention.

Expression Vectors Encoding NFIF Polypeptides

The identified and isolated DNA sequence can be inserted into an appropriate cloning/expression vector (hereinafter "vector") to facilitate modifications to the sequence or expression of the protein. These vectors typically include multiple cloning sites, promoters, sequences which facilitate replication in a host cell and selection markers.

Any suitable vector can be used. There are many known in the art. Examples of vectors that can be used include, for example, plasmids or modified viruses. The vector is typically compatible with a given host cell into which the vector is introduced to facilitate replication of the vector and expression of the encoded proteins. The insertion of a DNA sequence into a given vector can, for example, be accomplished by ligating the DNA fragment into a cloning vector which has complementary cohesive termini. However, if the complementary restriction sites used to cut the DNA are not present in the cloning vector, the ends of the DNA molecules may be enzymatically modified. Alternatively, any site desired may be produced by ligating nucleotide sequences (linkers) onto the DNA termini; the ligated linkers may comprise specific chemically synthesized oligonucleotides encoding restriction endonuclease recognition sequences. Useful vectors may consist of segments of chromosomal, non-chromosomal and synthetic DNA sequences. Examples of specific vectors useful in the practice of the present invention are E. coli bacteriophages, for example, lambda derivatives, or plasmids, for example, pBR322 derivatives or pUC plasmid derivatives, e.g., pmal-c, pFLAG, derivatives of SV40 and known bacterial plasmids, e.g., E. coli plasmids col E1, pCR1, pMal-C2, pET, pGEX (Smith et al., 1988, Gene 67:31-40), pMB9 and their derivatives, plasmids such as RP4; phage DNAs, e.g., the numerous derivatives of phage 1, e.g., NM989, and other phage DNA, e.g., M13 and filamentous single stranded phage DNA; yeast vectors such as the 2 μm plasmid or derivatives thereof; vectors useful in eukaryotic cells, for example, vectors useful in insect cells, such as baculovirus vectors, vectors useful in mammalian cells; vectors derived from combinations of plasmids and phage DNAs, plasmids that have been modified to employ phage DNA or other expression control sequences; and the like.

Examples of yeast vectors that can be used according to the invention are the non-fusion pYES2 vector (Invitrogen) or the fusion pYESHisA, B, C (Invitrogen).

Baculovirus vectors that can be used in the practice of the invention include a variety of vectors, including both non-fusion transfer vectors, for example, pVL941 (Summers), pVL1393 (Invitrogen), pVL1392 (Summers and Invitrogen), and pBlueBacIII (Invitrogen), and fusion transfer vectors, for example, pAc700 (Summers), pAc701 and pAc702, pAc360 (Invitrogen), and pBlueBacHisA, B, C (Invitrogen) can be used.

Mammalian vectors contemplated for use in the invention include, for example, vectors with inducible promoters, for example, the dihydrofolate reductase (DHFR) promoter, e.g., any expression vector with a DHFR expression vector, or a DHFR/methotrexate co-amplification vector, for example, pED (see Kaufman, *Current Protocols in Molecular Biology*, 16.12 (1991)). Alternatively, a glutamine synthetase/methionine sulfoximine co-amplification vector, for example, pEE14 (Celltech). In another embodiment, a vector that directs episomal expression under control of Epstein Barr Virus (EBV) can be used, for example, pREP4 (Invitrogen), pCEP4 (Invitrogen), pMEP4 (Invitrogen), pREP8 (Invitrogen), pREP9 (Invitrogen), and pEBVHis (Invitrogen). Selectable mammalian expression vectors for use in the invention include pRc/CMV (Invitrogen), pRc/RSV (Invitrogen), pcDNA3 (Invitrogen) and others. Vaccinia virus mammalian expression vectors (see, Kaufman, 1991, supra) for use according to the invention include but are not limited to pSC11, pMJ601, and pTKgptF1S.

A variety of methods may be used to confirm that the desired DNA sequence encoding NFIF-14b, NFIF-7a, or another NFIF variant, has been cloned into a vector. In general, one or more of the following approaches is used: (a) PCR amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding NFIF is inserted within the "selection marker" gene sequence of the vector, recombinants containing the NFIF insert can be identified by the absence of the selection marker gene function. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

Promoters

The nucleotide sequence coding for NFIF-14b or NFIF-7a or a NFIF variant thereof can be inserted into an expression vector which contains the necessary elements for the transcription and translation of the inserted protein-coding sequence. Such elements are termed herein a "promoter."

A promoter is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The nucleic acid encoding the polypeptides of the invention is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector or they may be supplied by the native gene encoding NFIF and/or its flanking regions. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression may be controlled by any promoter/enhancer element known in the art, but these regulatory elements must be functional in the host selected for expression. Examples of promoters which may be used to control NFIF gene expression include the SV40 early promoter region (Benoist and Chambon, 1981, *Nature* 290:304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42); prokaryotic expression vectors for example, the β-lactamase promoter (VIIIa-Kamaroff, et al., 1978, *Proc. Natl. Acad. Sci. U.S.A.*, 75:3727-s 3731), or the tac promoter (De- Boer, et al., 1983, *Proc. Natl. Acad. Sci. U.S.A.*, 80:21-25); promoter elements from yeast or other fungi, for example, the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, *Cell* 38:639-646; Ornitz et al., 1986, Cold Spring Harbor *Symp. Quant. Biol.*, 50:399-409; MacDonald, 1987, *Hepatology* 7:425-515); insulin gene control region which is active in pancreatic beta cells (Hanahan, 1985, *Nature* 315:115-122), immunoglobulin gene control region which is active in lymphoid cells (Grosschedl et al., 1984, *Cell* 38:647-658; Adames et al., 1985, *Nature* 318:533-538; Alexander et al., 1987, *Mol. Cell. Biol.*, 7:1436-1444), mouse mammary tumor virus control region which is active in testicular, breast, lymphoid and mast cells (Leder et al., 1986, *Cell* 45:485-495), albumin gene control region which is active in liver (Pinkert et al., 1987, *Genes and Devel.* 1:268-276), alpha-fetoprotein gene control region which is active in liver (Krumlauf et al., 1985, *Mol. Cell. Biol.*, 5:1639-1648; Hammer et al., 1987, *Science* 235:53-58), alpha 1-antitrypsin gene control region which is active in the liver (Kelsey et al., 1987, *Genes and Devel.*, 1:161-171), beta-globin gene control region which is active in myeloid cells (Mogram et al., 1985, *Nature* 315:338-340; Kollias et al., 1986, *Cell* 46:89-94), myelin basic protein gene control region which is active in oligodendrocyte cells in the brain (Readhead et al., 1987, *Cell* 48:703-712), myosin light chain-2 gene control region which is active in skeletal muscle (Sani, 1985, *Nature* 314:283-286), and gonadotropic releasing hormone gene control region which is active in the hypothalamus (Mason et al., 1986, *Science* 234:1372-1378).

A preferred promoter used in the expression vector constructs discussed hereinbelow is the cytomegalovirus (CMV) promoter which is capable of providing high level expression in a variety of mammalian cell lines.

Introduction of Vectors into Host Cells

Vectors can be introduced into host cells by any suitable method, including, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, *J. Biol. Chem.* 267:963-967; Wu and Wu, 1988, *J. Biol. Chem.* 263:14621-14624; Hartmut et al., Canadian Patent Application No. 2,012,311, filed Mar. 15, 1990) so that many copies of the gene sequence are generated.

In a preferred method, cells are transfected in vitro utilizing Lipfectamine7 available from Gibco-BRL. Preferably, the cloned gene is contained on a shuttle vector plasmid, which provides for expansion in a cloning cell, e.g., *E. coli*, and facilitates purification for subsequent insertion into an appropriate expression cell line. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 μm plasmid.

Host Cell Systems

Host cell systems include mammalian host cell systems, insect host cell systems and microorganisms such as yeast or bacteria. Depending on the host cell system utilized, any one of a number of suitable transcription and translation elements may be used.

In addition, a host cell strain may be chosen which modulates the expression of the inserted sequences or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. Expression in yeast can produce a biologically active product. Expression in eukaryotic cells can increase the likelihood of "native" folding. Moreover, expression in mammalian cells can provide a tool for reconstituting, or constituting, NFIF-inhibiting activity. Furthermore, different vector/host expression systems may affect processing reactions, such as proteolytic cleavages, to a different extent. Expression vectors of the invention can be used, as pointed out above, both to transfect cells for screening or biological testing of modulators of NFIF activity.

Examples of acceptable mammalian host cells are HEK 293 cells and COS-7 cells.

A recombinant NFIF-14b, NFIF-7a or NFIF variant of the invention may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding NFIF is introduced is cultured in an appropriate cell culture medium under conditions that provide for expression of an NFIF polypeptide by the cell.

Once a suitable host system and growth conditions are established, recombinant expression vectors can be propagated and prepared in quantity. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, including polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

As discussed above, a "vector" is any means for the transfer of a nucleic acid according to the invention into a host cell. Preferred vectors are viral vectors, for example, retroviruses, herpes viruses, adenoviruses, and adeno-associated viruses. Thus, a gene encoding a protein or polypeptide domain fragment of the present invention is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

The discussion which follows outlines various viral and non-viral systems that may be used to introduce DNA into a host cell in vivo or in vitro.

Viral Vector Systems

The NFIF polypeptides, as well as the antisense nucleic acids, ribozymes and antibodies discussed hereinbelow may be prepared in vitro or ex vivo or may be designed to be expressed in vivo in a patient using an appropriate expression system introduced via a viral vector system.

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsulating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Defective viruses, which entirely or almost entirely lack viral genes, are preferred. Defective virus is not replication competent after introduction into a cell, and thus does not lead to a productive viral infection. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., *Molec. Cell. Neurosci.* 2:320-330 (1991)), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (*J. Clin. Invest.* 90:626-630 (1992); see also La Salle et al., *Science* 259:988-990 (1993)); and a defective adeno-associated virus vector (Samulski et al., *J. Virol.* 61:3096-3101 (1987); Samulski et al., *J. Virol.* 63:3822-3828 (1989); Lebkowski et al., *Mol. Cell. Biol.* 8:3988-3996 (1988)])

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors. In addition, it is advantageous to employ a viral vector that is engineered to express a minimal number of antigens.

Naturally, the invention contemplates delivery of a vector that will express a therapeutically effective amount of NFIF for gene therapy applications. The phrase "therapeutically effective amount" is used herein to mean an amount sufficient to cause an improvement in a clinically significant condition in the host.

Certain viral vector systems are well developed in the art and are suited to the treatment methods of the present invention.

Adenovirus Vector Systems

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., *Virology* 75 (1990) 81), bovine, porcine, avian, and simian (example: SAV) origin.

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., *Gene* 101 (1991) 195, EP 185 573; Graham, *EMBO J.* 3 (1984) 2917). In particular, they can be prepared by homologous recombination between an adenovirus and a plasmid which carries, inter alia, the DNA sequence of interest. The homologous recombination is effected following cotransfection of the adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., *J. Gen. Virol.* 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-Associated Virus Vector Systems

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterised. It encompasses approximately 4700 bases and contains an inverted terminal repeat (ITR) region of approximately 145 bases at each end, which serves as an origin of replication for the virus. The remainder of the genome is divided into two essential regions which carry the encapsulation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsulation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid encoding NFIF or its variants flanked by the AAV ITRs. The invention also relates to a plasmid encompassing a sequence encoding a nucleic acid encoding NFIF or its variants flanked by two ITRs from an AAV. Such a plasmid can be used as it is for transferring the nucleic acid sequence, with the plasmid, where appropriate, being incorporated into a liposomal vector (pseudo-virus).

Retrovirus Vector Systems

In another embodiment the gene can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; EP 453242, EP178220; Bernstein et al. *Genet. Eng.* 7 (1985) 235; McCormick, *BioTechnology* 3 (1985) 689; International Patent Publication No. WO 95/07358, published Mar. 16, 1995, by Dougherty et al.; and Kuo et al., 1993, *Blood* 82:845. The retroviruses are integrating viruses which infect dividing cells. The retrovirus genome includes two LTRs, an encapsulation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsulation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsulation sequences which may include a part of the gag gene (Bender et al., *J. Virol.* 61 (1987) 1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Non-Viral Systems

Certain non-viral systems have been used in the art and can facilitate introduction of DNA encoding the NFIF polypeptides, antisense nucleic acids, ribozymes and antibodies.

Lipofection Delivery Systems

A vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al., *Proc. Natl. Acad. Sci. U.S.A.* 84:7413-7417 (1987); see Mackey, et al., *Proc. Natl. Acad. Sci. U.S.A.* 85:8027-8031 (1988); Ulmer et al., *Science* 259:1745-1748 (1993)). The use of cationic lipids may promote encapsulation of negatively charged nucleic acids, and also promote fusion with negatively charged cell membranes (Felgner and Ringold, *Science* 337:387-388 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, for example, pancreas, liver, kidney, and the brain. Lipids may be chemically coupled to other molecules for the purpose of targeting (see Mackey, et. al., supra). Targeted peptides, e.g., hormones or neurotransmitters, and proteins for example, antibodies, or non-peptide molecules could be coupled to liposomes chemically.

Other molecules are also useful for facilitating transfection of a nucleic acid in vivo, for example, a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Naked DNA Delivery Systems

It is also possible to introduce the vector in vivo as a naked DNA plasmid (see U.S. Pat. Nos. 5,693,622, 5,589,466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990; Williams et al., *Proc. Natl. Acad. Sci. USA* 88:2726-2730 (1991)). Receptor-mediated DNA delivery approaches can also be used (Curiel et al., *Hum. Gene Ther.* 3:147-154 (1992); Wu and Wu, *J. Biol. Chem.* 262: 4429-4432 (1987)).

Uses for NFIF Polypeptides

As mentioned above, in certain situations it is desirable to induce NFκB in order to initiate or increase the extent of an immune response. In order to induce NFκB, the NFIF polypeptides of the present invention can be introduced into the body of a patient by a variety of methods.

The methods used to introduce NFIF into a patient's body include direct administration of purified NFIF polypeptides or introduction of nucleic acid encoding NFIF polypeptides in expression vectors which express the polypeptides in the patient's body.

In embodiments involving direct administration of NFIF polypeptides, the NFIF polypeptides are prepared using the host cell expression systems such as those described above. The polypeptides are purified using conventional purification methods and then combined with a suitable biologically-compatible solution as described in detail below. The solution containing the polypeptide is introduced into the patient by topical, oral, parenteral, intranasal, subcutaneous or intraocular routes. Once in the body, the polypeptide is able to exert its effect, inducing NFκB and thereby resulting in an increase in the activity of NFκB-regulated pathways, including immune responses.

In embodiments involving administration of nucleic acids encoding NFIF polypeptides, viral or non-viral systems utilizing expression vectors capable of expressing NFIF polypeptides can be introduced into the patient's body. Any of the viral or non-viral transfection systems described above may be used. The viral and non-viral vector systems are also combined with an appropriate biologically-compatible solution to facilitate their introduction into the body. Once a viral or non-viral vector is introduced into the body, the NFIF polypeptide encoding nucleic acid may integrate into the host's genome, providing stable, long-term expression of NFIF polypeptides which exert their effect as described above. Transient expression may be provided by systems that introduce the nucleic acid into cells, but do not integrate into the genome.

The NFIF-14b and NFIF-7a polypeptides contain signal sequences, indicating these polypeptides are capable of being expressed in one cell while exerting their effect in another cell. Accordingly, the NFIF polypeptides may be expressed by cells that then release NFIF polypeptide into the bloodstream or other transport system (lymph, etc.) where they are transported to tissues where they exert their effect on NFκB induction.

The discussion which follows describes how to identify compositions and methods for regulating NFκB induction based on the present discovery of the NFIF polypeptides.

Compositions

The present invention provides compositions in a biologically compatible (biocompatible) solution comprising the polypeptides, nucleic acids, and vectors of the invention. A biologically compatible solution is a solution in which the polypeptide, nucleic acid or vector of the invention is maintained in an active form, e.g., in a form able to effect a biological activity. For example, a polypeptide of the invention could have NFκB activation or deactivation activity; an antibody (which is itself a polypeptide) would bind a polypeptide of the invention; a nucleic acid would be able to replicate, translate a message, or hybridize to a complementary nucleic acid; and a vector would be able to transfect a target cell. Generally, such a biologically compatible solution will be an aqueous buffer, e.g., Tris, phosphate, or HEPES buffer, containing salt ions. Usually the concentration of salt ions will be similar to physiological levels. In a specific embodiment, the biocompatible solution is a pharmaceutically acceptable composition. Biologically compatible solutions may include stabilizing agents and preservatives.

Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well known nontoxic physiologically acceptable carriers, adjuvants and vehicles as desired.

The preferred sterile injectable preparations can be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available. A hydrogel can be deposited directly onto the surface of the tissue to be treated, for example, during surgical intervention.

Another preferred embodiment of the present invention relates to a pharmaceutical composition comprising a replication defective recombinant virus and poloxamer. More specifically, the invention relates to a composition comprising a replication defective recombinant virus comprising a nucleic acid encoding an NFIF polypeptide and poloxamer. A preferred poloxamer is Poloxamer 407, which is commercially available (BASF, Parsippany, N.J.) and is a non-toxic, biocompatible polyol, and is most preferred. A poloxamer impregnated with recombinant viruses may be deposited directly on the surface of the tissue to be treated, for example during a surgical intervention. Poloxamer possesses essentially the same advantages as a hydrogel while having a lower viscosity.

The present invention also relates to compositions useful in the manufacture of medicaments intended for the treatment of subjects affected with an NFκB-regulated inflammatory response and compositions useful in the manufacture of medicaments intended to prevent subjects from being affected with an NFκB-regulated inflammatory response. Accordingly, the present invention includes the use of an NFIF polypeptide according to the invention for the manufacture of a medicament intended for the treatment and/or prevention of an NFκB-regulated inflammatory response. The present invention also includes the use of a nucleic acid according to the invention, encoding an NFIF polypeptide, for the manufacture of a medicament intended for the treatment and/or prevention of an NFκB-regulated inflammatory response. The present invention further includes the use of a recombinant vector according to the invention, comprising a nucleic acid encoding an NFIF polypeptide, for the manufacture of a medicament intended for the treatment and/or prevention of an NFκB-regulated inflammatory response. The present invention also includes the use of a defective recombinant viral vector according to the invention for the manufacture of a medicament intended for the treatment and/or prevention of an NFκB-regulated inflammatory response.

Another aspect of the present invention relates to the use of compositions comprising cells genetically modified ex vivo with a recombinant virus and compositions comprising cells containing such recombinant viruses which are implanted in the body, facilitating prolonged and effective expression in vivo of an NFIF polypeptide according to the invention.

Therapeutic Compounds Based on NFIF that Inhibit Activation of NFκB

As explained above, in certain situations, it is desirable to reduce or inhibit NFκB-regulated immune responses. By inhibiting the expression of the NFIF gene or interfering with the activity of NFIF polypeptides, it is possible to inhibit induction of NFκB and consequently inhibit or prevent NFκB-regulated immune responses that result in atherosclerosis and other diseases.

There are a variety of therapeutic compounds which may be used to inhibit NFIF expression or activity. These therapeutic compounds may be nucleic acids, polypeptides, peptides or non-peptide small molecules. In one embodiment, antisense nucleic acids are used to decrease expression of the NFIF gene by inhibiting processing (splicing) of the NFIF primary transcript. In another embodiment, ribozymes that cleave NFIF mRNA are used, preventing the synthesis of NFIF. Polypeptides of the present invention include antibodies or other binding proteins that bind NFIF polypeptides and interfere with their ability to activate NFκB induction. In addition, compounds such as small molecule inhibitors which inhibit NFIF gene expression or the activity of NFIF polypeptides can be identified in reporter gene assays as described above and administered to patients to inhibit NFIF expression/activity. The same methods described above for introducing NFIF polypeptides and nucleic acids encoding NFIF polypeptides into a patient's body are used to administer the various anti-NFIF compositions.

Antisense Nucleic Acids

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding NFIF or the corresponding messenger RNA. In addition, antisense nucleic acids may be designed or identified which decrease expression of the NFIF gene by inhibiting splicing of its primary transcript. With knowledge of the structure and partial sequence of the NFIF gene, such antisense nucleic acids can be designed and tested for efficacy.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (Rnase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its target site. Modifications may include 2' deoxy, O-pentoxy, O-propoxy, O-methoxy, fluoro, methoxyethoxy phosphoro-thioates, modified bases, as well as other modifications known to those of skill in the art.

The antisense nucleic acids can also be DNA sequences whose expression in the cell produces RNA complementary to all or part of the NFIF mRNA. Antisense nucleic acids can be prepared by expression of all or part of a sequence selected from the group consisting of the sequence in FIG. 3, in the opposite orientation, as described in EP 140308. Any length of antisense sequence is suitable for practice of the invention so long as it is capable of down-regulating or blocking expression of NFIF. Preferably, the antisense sequence is at least 20 nucleotides in length. The preparation and use of antisense nucleic acids, DNA encoding antisense RNAs and the use of oligo and genetic antisense is disclosed in WO92/15680, the contents of which are incorporated herein by reference.

One approach to determining the optimum fragment of NFIF to use in an antisense nucleic acid treatment method involves preparing random fragments of NFIF cDNA by mechanical shearing, enzymatic treatment, and cloning the fragment into any of the vector systems described herein. Individual clones or pools of clones are used to infect NFIF-expressing cells, and effective antisense NFIF cDNA fragments are identified by monitoring NFIF expression at the RNA or protein level.

The retroviral, adeno-associated viral, and adenoviral vector systems discussed hereinabove may all be used to introduce and express antisense nucleic acids in cells. Antisense synthetic oligonucleotides may be introduced in a variety of ways, including the methods discussed hereinbelow.

Ribozymes

Reductions in the levels of NFIF polypeptide may be accomplished using ribozymes. Ribozymes are catalytic RNA molecules (RNA enzymes) that have separate catalytic and substrate binding domains. The substrate binding sequence combines by nucleotide complementarity and, possibly, nonhydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base-pairing. Once it is bound to the correct target site, the ribozyme acts enzymatically to cut the target mRNA. Cleavage of the NFIF mRNA by a ribozyme destroys its ability to direct synthesis of NFIF polypeptide. Once the ribozyme has cleaved its target sequence, it is released and can repeatedly bind and cleave at other NFIF mRNAs.

Examples of ribozymes for use in the practice of the present invention include a variety of motifs, for example, hammerhead motif, hairpin motif, a hepatitis delta virus, group I intron or RnaseP RNA (in association with an RNA guide sequence) motif or *Neurospora* VS RNA motif. Hammerhead motifs are described by Rossi et al., 1992, *Aids Research and Human Retroviruses*, 8, 183. Hairpin motifs are described in Hampel and Tritz, 1989, *Biochemistry*, 28, 4929, and Hampel et al., 1990, *Nucleic Acids Res.*, 18, 299. The hepatitis delta virus motif is described by Perrotta and Been, 1992, *Biochemistry*, 31, 16, the RnaseP motif is described by Guerrier-Takada et al., 1983, *Cell*, 35, 849, the *Neurospora* VS RNA ribozyme motif is described by Collins (Saville and Collins, 1990, *Cell*, 61, 685-696; Saville and Collins, 1991, *Proc. Natl. Acad. Sci. USA*, 88, 8826-8830; Collins and Olive, 1993, *Biochemistry*, 32, 2795-2799) the Group I intron motif is described by Cech et al., U.S. Pat. No. 4,987,071.

One approach in preparing a ribozyme is to synthesize chemically an oligodeoxyribonucleotide with a ribozyme catalytic domain (~20 nucleotides) flanked by sequences that hybridize to the target NFIF mRNA after transcription. The oligodeoxyribonucleotide is amplified by using the substrate binding sequences as primers. The amplification product is cloned into a eukaryotic expression vector.

Ribozymes possessing a hammerhead or hairpin structure are prepared readily since these catalytic RNA molecules can be expressed within cells from eukaryotic promoters (e.g., Scanlon et al., 1991, *Proc. Natl. Acad. Sci. USA*, 88, 10591-5; Kashani-Sabet et al., 1992, *Antisense Res. Dev.*, 2, 3-15; propulic et al., 1992, *J. Virol.*, 66, 1432-41; Weerasinghe et al., 1991, *J. Virol.*, 65, 5531-4; Ojwang et al., 1992, *Proc. Natl. Acad. Sci. USA*, 89, 10802-6; Chen et al., 1992, *Nucleic Acids Res.*, 20, 4581-9; Sarver et al., 1990, *Science*, 247, 1222-1225)). A ribozyme of the present invention can be expressed in eukaryotic cells from the appropriate DNA vector. If desired, the activity of the ribozyme may be augmented by its release from the primary transcript by a second ribozyme (Ohkawa et al., 1992, *Nucleic Acids Symp. Ser.*, 27, 15-6; Taira et al., 1991, *Nucleic Acids Res.*, 19, 5125-30; Ventura et al., 1993, *Nucleic Acids Res.*, 21, 3249-55).

In one approach to preparing ribozymes, ribozymes are expressed from transcription units inserted into DNA, RNA, or viral vectors. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA*, 87, 6743-7; Gao and Huang 1993, *Nucleic Acids Res.*, 21, 2867-72; Lieber et al., 1993, *Methods Enzymol.*, 217, 47-66; Zhou et al., 1990, *Mol. Cell. Biol.*, 10, 4529-37). It has been demonstrated that ribozymes expressed from these promoters can function in mammalian cells (Kashani-Sabet et al., 1992, *Antisense Res. Dev.*, 2, 3-15; Ojwang et al., 1992, *Proc. Natl. Acad. Sci. USA*, 89, 10802-6; Chen et al., 1992 *Nucleic Acids Res.*, 20, 4581-9; Yu et al., 1993, *Proc. Natl. Acad. Sci. USA*, 90, 6340-4; L'Huillier et al., 1992, *EMBO J.*, 11, 4411-8; Lisziewicz et al., 1993, *Proc. Natl. Acad. Sci. USA*, 90, 8000-4).

In one embodiment of the present invention, a transcription unit expressing a ribozyme that cleaves NFIF RNA is inserted into a plasmid DNA vector, a retrovirus vector, an adenovirus DNA viral vector or an adeno-associated virus vector. The recombinant vectors are preferably DNA plasmids or adenovirus vectors. However, other mammalian cell vectors that direct the expression of RNA may be used for this purpose. The vectors are delivered as recombinant viral particles. DNA may be delivered alone or complexed with various vehicles. The DNA, DNA/vehicle complexes, or the recombinant virus particles are locally administered to the site of treatment, as discussed below. Preferably, recombinant vectors capable of expressing the ribozymes are locally delivered as described below, and persist in target cells. Once expressed, the ribozymes cleave the target NFIF mRNA.

Ribozymes may be administered to a patient by a variety of methods. They may be added directly to target tissues, complexed with cationic lipids, packaged within liposomes, or delivered to target cells by other methods known in the art. Localized administration to the desired tissues may be done by catheter, infusion pump or stent, with or without incorporation of the ribozyme in biopolymers as discussed hereinbelow. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. More detailed descriptions of ribozyme delivery and administration are provided in Sullivan et al., PCT WO94/02595 and Draper et al., PCT WO93/23569, which are incorporated by reference herein.

Antibodies

The present invention provides antibodies against the NFIF polypeptide. These antibodies may be monoclonal antibodies or polyclonal antibodies. The present invention includes chimeric, single chain, and humanized antibodies, as well as Fab fragments and the products of an Fab expression library, and Fv fragments and the products of an Fv expression library.

Polyclonal antibodies may be prepared against an antigenic fragment of an NFIF polypeptide. Antibodies may also be generated against the intact NFIF protein or polypeptide, or against a fragment, derivative, or epitope of the protein or polypeptide. Antibodies may be obtained following the administration of the protein, polypeptide, fragment, derivative, or epitope to an animal, using the techniques and procedures known in the art.

Monoclonal antibodies may be prepared using the method of Mishell, B. B., et al., Selected Methods In Cellular Immunology, (W.H. Freeman, ed.) San Francisco (1980). Briefly, a polypeptide of the present invention is used to immunize spleen cells of Balb/C mice. The immunized spleen cells are fused with myeloma cells. Fused cells containing spleen and myeloma cell characteristics are isolated by growth in HAT medium, a medium which kills both parental cells, but allows the fused products to survive and grow.

The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. G. E. Mark and E. A. Padlan, "Chapter 4. Humanization of Monoclonal Antibodies", The Handbook of Experimental Pharmacology Vol. 113, Springer-Verlag, New York, 1994). Transgenic animals may be used to express humanized antibodies.

Techniques known in the art for the production of single chain antibodies can be adapted to produce single chain antibodies to the immunogenic polypeptides and proteins of the present invention.

In a preferred embodiment, an anti-NFIF antibody is used to bind to and inhibit the activity of NFIF in a patient.

The anti-NFIF antibodies are also useful in assays for detecting or quantitating levels of NFIF. In one embodiment, these assays provide a clinical diagnosis and assessment of NFIF in various disease states and a method for monitoring treatment efficacy. An example of an anti-NFIF antibody used to bind NFIF and identify its presence in tissues is provided in Example 5. These anti-NFIF antibodies may additionally be used to quantitate NFIF in a tissue sample.

Methods of Treatment

The present invention provides methods of treatment which comprise the administration to a human or other animal of an effective amount of a composition of the invention.

Effective amounts may vary, depending on the age, type and severity of the condition to be treated, body weight, desired duration of treatment, method of administration, and other parameters. Effective amounts are determined by a physician or other qualified medical professional. In most cases, the dosage levels may be adjusted so that the desired levels of NFIF or other therapeutic compounds can be achieved and maintained.

Polypeptides according to the invention are generally administered in doses of about 0.01 mg/kg to about 100 mg/kg, more preferably about 0.1 mg/kg to about 50 mg/kg, and even more preferably about 1 mg/kg to about 10 mg/kg of body weight per day.

Neutralizing antibodies according to the invention may be delivered as a bolus only, infused over time or both administered as a bolus and infused over time. Although the dosage amount will vary based on the parameters above, and on the binding ability of the antibody, a dose 0.2 to 0.6 mg/kg may be given as a bolus followed by a 2 to 12 hour infusion period. Alternatively, multiple bolus injections are administered every other day or every third or fourth day as needed. Dosage levels may be adjusted as determined by NFIF levels and/or NFκB induction levels.

As discussed hereinabove, recombinant viruses may be used to introduce both DNA encoding NFIF and subfragments of NFIF as well as antisense nucleic acids. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

Ribozymes according to the present invention may be administered in amounts ranging from about 5 to about 50 mg/kg/day in a pharmaceutically acceptable carrier. Dosage levels may be adjusted based on the measured therapeutic efficacy.

Appropriate levels of inhibitor or enhancer molecules may be determined by qualified medical personnel using the parameters discussed above.

Methods for Increasing the Level of NFIF Polypeptide Activity

The methods for increasing the expression or activity of NFIF polypeptide include, but are not limited to, administration of a composition comprising the NFIF polypeptide, administration of a composition comprising an expression vector which encodes the NFIF polypeptide, administration of a composition comprising an enhancer molecule which enhances the activity of the NFIF polypeptide and administration of an enhancer molecule which increases expression of the NFIF gene.

Methods Utilizing NFIF Polypeptides

In one embodiment, the level of NFIF activity is increased through the administration of a composition comprising the NFIF polypeptide. This composition may be administered in a convenient manner, such as by the oral, topical, intravenous, intraperitoneal, intramuscular, subcutaneous, intranasal, or intradermal routes. The composition may be administered directly or it may be encapsulated (e.g. in a lipid system, in amino acid microspheres, or in globular dendrimers). The polypeptide may, in some cases, be attached to another polymer such as serum albumin or polyvinyl pyrrolidone.

Methods Utilizing Vectors that Express NFIF

In another embodiment, the level of NFIF is increased through the use of gene therapy, that is, through the administration of composition comprising a nucleic acid which encodes and directs the expression of the NFIF polypeptide. In this embodiment, the NFIF polypeptide is cloned into an appropriate expression vector. Possible vector systems and promoters are extensively discussed above. The expression vector is transferred into the target tissue using one of the vector delivery systems discussed above. This transfer is carried out either ex vivo in a procedure in which the nucleic acid is transferred to cells in the laboratory and the modified cells are then administered to the human or other animal, or in vivo in a procedure in which the nucleic acid is transferred directly to cells within the human or other animal. In preferred embodiments, an adenoviral vector system is used to deliver the expression vector. If desired, a tissue specific promoter is utilized in the expression vector as described above.

Non-viral vectors may be transferred into cells using any of the methods known in the art, including calcium phosphate coprecipitation, lipofection (synthetic anionic and cationic liposomes), receptor-mediated gene delivery, naked DNA injection, electroporation and bioballistic or particle acceleration.

Methods Utilizing an Enhancer Molecule which Enhances the Activity of NFIF

In another embodiment, the activity of NFIF is enhanced by enhancer molecules that increase the activity of NFIF or increase its appropriate recognition by cellular binding sites. These enhancer molecules may be introduced by the same methods discussed above for the administration of polypeptides.

Methods Utilizing an Enhancer Molecule which Increases NFIF Gene Expression

In another embodiment, the level of NFIF is increased through the use of small molecular weight compounds, which can upregulate NFIF expression at the level of transcription, translation, or post-translation. These compounds may be administered by the same methods discussed above for the administration of polypeptides.

Methods for Treating or Preventing an NFκB-Regulated Inflammatory Response

The present invention includes methods for the treatment or prevention of NFκB-regulated inflammatory responses including, but not limited to, rheumatoid arthritis, atherosclerosis, autoimmune diseases, viral diseases, NSAID-induced gastropathy, neurodegenerative diseases, scrapie, sepsis, apoptosis, Crohn's disease, renal disease, restenosis, brain injury/inflammation, Alzheimer's disease, asthma, and improperly regulated expression of pleiotropic cytokines These methods include, but are not limited to, administration of a composition comprising an antisense nucleic acid, administration of a composition comprising an intracellular binding protein such as an antibody, administration of an inhibitory molecule which inhibits the activity of NFIF, for example, a composition comprising an expression vector encoding a subfragment of NFIF or a small molecular weight molecule, including administration of a small molecular weight compound which down regulates NFIF expression at the level of transcription, translation or post-translation, administration of a ribozyme which cleaves mRNA encoding NFIF, administration of a medicament manufactured using an NFIF polypeptide, administration of a medicament manufactured using a nucleic acid encoding an NFIF polypeptide, administration of a medicament manufactured using a recombinant vector which includes nucleic acid encoding an NFIF polypeptide and administration of a medicament manufactured using a defective recombinant viral vector which includes nucleic acid encoding an NFIF polypeptide.

Methods for Lowering Levels of NFIF Polypeptide Activity

The methods for decreasing the expression of NFIF polypeptide in order to decrease NFκB induction include, but are not limited to, administration of a composition comprising an antisense nucleic acid, administration of a composition comprising an intracellular binding protein such as an antibody, administration of an inhibitory molecule which inhibits the activity of NFIF, for example, a composition comprising an expression vector encoding a subfragment of NFIF or a small molecular weight molecule, including administration of a small molecular weight compound which down regulates NFIF expression at the level of transcription, translation or post-translation, and administration of a ribozyme which cleaves mRNA encoding NFIF.

Methods Utilizing Antisense Nucleic Acids

In one embodiment, a composition comprising an antisense nucleic acid is used to down-regulate or block the expression of NFIF. In one preferred embodiment, the nucleic acid encodes antisense RNA molecules. In this embodiment, the nucleic acid is operably linked to signals enabling expression of the nucleic acid sequence and is introduced into a cell utilizing, preferably, recombinant vector constructs, which will express the antisense nucleic acid once the vector is introduced into the cell. Examples of suitable vectors includes plasmids, adenoviruses, adeno-associated viruses, retroviruses, and herpes viruses. Preferably, the vector is an adenovirus. Most preferably, the vector is a replication defective adenovirus comprising a deletion in the E1 and/or E3 regions of the virus.

In another embodiment, the antisense nucleic acid is synthesized and may be chemically modified to resist degradation by intracellular nucleases, as discussed above. Synthetic antisense oligonucleotides can be introduced to a cell using liposomes. Cellular uptake occurs when an antisense oligonucleotide is encapsulated within a liposome. With an effective delivery system, low, non-toxic concentrations of the antisense molecule can be used to inhibit translation of the target mRNA. Moreover, liposomes that are conjugated with cell-specific binding sites direct an antisense oligonucleotide to a particular tissue.

Methods Utilizing Neutralizing Antibodies and Other Binding Proteins

In another embodiment, the expression of NFIF is down-regulated or blocked by the expression of a nucleic acid sequence encoding an intracellular binding protein which is capable of selectively interacting with NFIF. WO 94/29446 and WO 94/02610, the contents of which are incorporated herein by reference, disclose cellular transfection with genes encoding an intracellular binding protein. An intracellular binding protein includes any protein capable of selectively interacting, or binding, with NFIF in the cell in which it is expressed and of neutralizing the function of bound NFIF. Preferably, the intracellular binding protein is a neutralizing antibody or a fragment of a neutralizing antibody. More preferably, the intracellular binding protein is a single chain antibody.

WO 94/02610 discloses preparation of antibodies and identification of the nucleic acid encoding a particular antibody. Using NFIF or a fragment thereof, a specific monoclonal antibody is prepared by techniques known to those skilled in the art. A vector comprising the nucleic acid encoding an intracellular binding protein, or a portion thereof, and capable of expression in a host cell is subsequently prepared for use in the method of this invention.

Alternatively, NFIF activity can be blocked by administration of a neutralizing antibody into the circulation. Such a neutralizing antibody can be administered directly as a protein, or it can be expressed from a vector (with a secretory signal).

Methods Utilizing an Inhibitory Molecule which Prevents NFIF Gene Expression

In another embodiment, inhibitory molecules, including small molecular weight compounds, are able to down regulate NFIF expression at the level of transcription, translation or post-translation. In order to identify such inhibitory molecules, the reporter gene systems described above may be used. These inhibitory molecules may be combined with a pharmaceutically acceptable carrier and administered using conventional methods known in the art.

Methods Utilizing Ribozymes

Ribozymes may be administered to cells by encapsulation in liposomes, by iontophoresis, by incorporation into hydrogels, cyclodextrins, biodegradable nanocapsules, and bioadhesive microspheres or by any of a variety of other methods discussed above. The ribozyme may be delivered to a target tissue by direct injection or by use of a catheter, infusion pump or stent. Alternative routes of delivery include intravenous injection, intramuscular injection, subcutaneous injection, aerosol inhalation, oral (tablet or pill form), topical, systemic, ocular, intraperitoneal and/or intrathecal delivery.

In preferred embodiments, a ribozyme-encoding sequence is cloned into a DNA expression vector. Transcription of the ribozyme sequence is driven from an eukaryotic RNA polymerase II (pol II), or RNA polymerase III (pol III) promoter. The expression vector can be incorporated into a variety of vectors including the viral DNA vectors such as adenovirus or adeno-associated virus vectors discussed above.

In a preferred embodiment of the invention, a transcription unit expressing a ribozyme that cleaves NFIF RNA is inserted into an adenovirus DNA viral vector. The vector is delivered as recombinant viral particles and is locally administered to the site of treatment, through the use of a catheter, stent or infusion pump.

EXAMPLES

Example 1

Method for Cloning NFIF-14b and NFIF-7a

To isolate the DNA encoding NFIF-14b and NFIF-7a, a cDNA library was prepared from human vascular smooth muscle cell (SMC) total RNA using a Clontech Marathon™ cDNA library synthesis kit. The cDNA synthesis kit also includes a control human placenta DNA library. The libraries are linear and amplifiable by PCR.

The NFIF-14b and NFIF-7a genes were obtained by PCR performed on both Human Vascular SMC and Human Placenta cDNA marathon libraries.

To perform the PCR reactions, standard PCR components [Perkin Elmer 10× buffer and Taq Gold Polymerase] were used and the reaction was performed as follows. The reaction mixtures were heated to 94° C. for 10 minutes, then thermocycled 10 times with a denaturing step of 94° C. for 30 seconds, an annealing step of 65° C. for 30 seconds, and an extension step of 72° C. for 1.5 minutes. Following these ten cycles, the reaction was thermocycled 30 times with a denaturing step of 94° C. for 30 seconds, an annealing step of 46° C. for 30 seconds, and an extension step of 72° C. for 1.5 minutes. Following these 30 cycles, the reactions were incubated at 72° C. for 7 minutes and stored at 4° C. The PCR reactions were performed in a Perkin Elmer 9600 thermocycler.

The PCR product from each PCR was ligated into pCR2.1 (Invitrogen) and transformed in DH5α-*E. coli*. Clones were picked and grown up in 5 ml of LB-amp; plasmids were then isolated and digested with EcoRI to check for the size of the released insert. Five out of fifteen clones gave bands of size 1.2-1.3 Kb, suggestive of the target gene and were sequenced.

Putative NFIF clones were identified based on an open reading frame and sequence alignment of the sequence against a predicted 5' sequence. Clones Nos. 14b and 7a were chosen for further characterization.

Large plasmid preparations were grown up from original glycerol stocks of clone 7 and 14, and isolated using a Qiagen MaxiPrep Kit.

Example 2

Subcloning of Clone 7a and 14b into a Eukaryotic Expression Vector

Clones 14b and 7a were further subcloned into the plasmid vector pCDNA3.1myc-his available from Invitrogen. This expression vector includes a strong promoter for high level expression in mammalian cells and a selection marker for generating stable cell lines. A C-terminal fusion tag in the vector features a polyhistidine sequence for rapid purification and a myc epitope for convenient detection with an anti-myc antibody.

PCR reactions were performed using PCR primers
5' hasm-5'-tccaccatggcgctggtgcgcgcactc-3' (SEQ ID NO.: 6) and
fushasm3'-3'-ctggatatcgtaattgtgctttatataaagctg-5'(SEQ ID NO.: 7) and the pCR2.1 construct for each full length clone as template. PCR conditions using 475 pg of pCR2.1 clone 7a or 500 pg of pCR2.1 clone 14b were as follows: the reaction mixtures were heated to 95° C. for 10 minutes, then thermocycled 30 times with a denaturing step of 95° C. for 30 seconds, an annealing step of 52° C. for 30 seconds, and then an extension step of 72° C. for 1.5 minutes. Following these 30 cycles, the reactions were incubated at 72° C. for 7 minutes, and stored at 4° C.

The PCR product was ligated into pCR2.1 and the insert DNA sequenced utilizing a Big Dye Terminator Cycle Sequencing Ready Reaction and a Perkin Elmer Applied Biosystems ABI Prism 377 DNA Sequencer. Sequencing demonstrated that the PCR primer removed the natural stop codon (TAG) and introduced an EcoRV site.

The positive constructs of NFIF-14b and -7a were digested with EcoRI and EcoRV and subcloned into pCDNA3.1 mychis (Invitrogen) cut with EcoRI and EcoRV. This resulted in the myc tag being fused to the 3' end of the NFIF cDNAs. These constructs were called pCDNA3.1mychasm7a and pCDNA3.1hasm14bmyc.

Example 3

Preparation of Deletion Variants of NFIF

Deletion mutants of NFIF-14b and NFIF-7a were prepared by PCR reactions using the pCDNA3.1mychasm7a and pCDNA3.1hasm14bmyc plasmids described above. Two sets of PCR primers were used to prepare the deletion mutants:

```
hasm313mut + hasm3'mut:
                                   (SEQ ID NO.: 8)
   5' gctccaccatgatatggacaggggatag 3'

(SEQ ID NO.: 9)
   5' gccactgtgctggatatcgtaattaac 3' hasm396mut + hasm3'mut:
                                   (SEQ ID NO.: 10)
   5' gctccaccatgacaaccaccatccagagtc 3'

(SEQ ID NO.: 9)
   5' gccactgtgctggatatcgtaattaac 3'
```

The hasm313+hasm3' mut primer pair produced the identical sequence of the full length clone 14b or 7a cDNAs but on an open reading frame initiated downstream at bp313 (ATG). (Numbering is from the ATG in the full length clone.) The consensus Kozak sequence was included in the forward primer to optimize translation.

The hasm396+hasm3' mut primer pair produced the identical sequence of the full length cDNAs but on an open reading frame initiated downstream at by 394 (ATG).

The PCR products were ligated into pCR2.1 and the insert DNA sequenced. Each deletion mutant was cut with EcoRI/EcoRV and subcloned into pCDNA3.1mychis cut with EcoRI and EcoRV. NFIF-14b deletion clones with the correct sequence were named pCDNAmychis 14-313 and pCDNA-mychis 14-396. NFIF-7a deletion clones with the correct sequence were named pCDNAmychis 7-313, and pCDNAmychis 7-396.

Analysis of the above clones using in vitro transcription/translation incorporating [$^{35}$S methionine] into the reaction [Promega TnT Quick Coupled Transcription Translation kit # L1170] produced bands of the size expected (NFIF 14b=51 kDa; NFIF 14-313=40 kDa; NFIF 14-396=37 kDa; NFIF 7a=41 kDa; NFIF 7-313=30 kDa; and NFIF 7-396=27 kDa) for shortened open reading frames. The facility of translation was important to determine before assessing functional activity and determining which domains were important for activity.

Example 4

Method for Transfecting Cells with NFIF-14b or NFIF-7a to Produce Stable Cell Lines Containing Plasmids To prepare stable cell lines containing NFIF-14b, NFIF-7a and the deletion mutants, Falcon 6 well plates were seeded with $2 \times 10^5$ HEK293 or COS-7 cells, the finalized cDNA NFIF constructs pCDNAmychis7, pCDNAmychis7-313, pCDNAmychis7-396; pCDNAmychis14, pCDNAmychis14-313, pCDNAmychis14-396 (0.8 ug) along with the Stratagene pNFκB-Luc reporter gene vector (0.1 ug) and Clontech EGFP vector (0.1 ug), were transfected using 6 ul Lipofectamine and 200 ul Optimem into the 6 well plates (with 800 ul fresh Optimem/well). The transfection was incubated for 4 hr at 37° C. and then the plates were fed with complete media (3 ml).

At 24, 48 and 72 hours post transfection lysates were made using 200 ul 1× Reporter Lysis Buffer solution (E397A-Promega). Lysates were incubated for 20 minutes on ice, vortexed, then centrifuged at 12,000 rpm for 5 minutes The supernatant was used to assess luciferase activity per the instructions in the Stratagene pNFκB-luc reporter gene kit.

To prepare stable cells lines, duplicates of the above 48 hr cultures were split at a 1:100 ratio into complete growth media along with G418 for selection of cells incorporating the plasmids in their DNA. Single cell clones were isolated and transferred into 48 well culture dishes for growout. Clones were chosen according to their activity in the NFκB luciferase reporter assay.

Luciferase activity was measured from the cell lysates of all the transient infected cell lines. 20 µl of lysate was added to a 96 well Costar serocluster (#3789) white round bottom plate. 100 µl of Luciferase Reagent (Promega E1501) was added directly before reading the sample in a 1450 Microbeta Walko jet.

Figure 6:
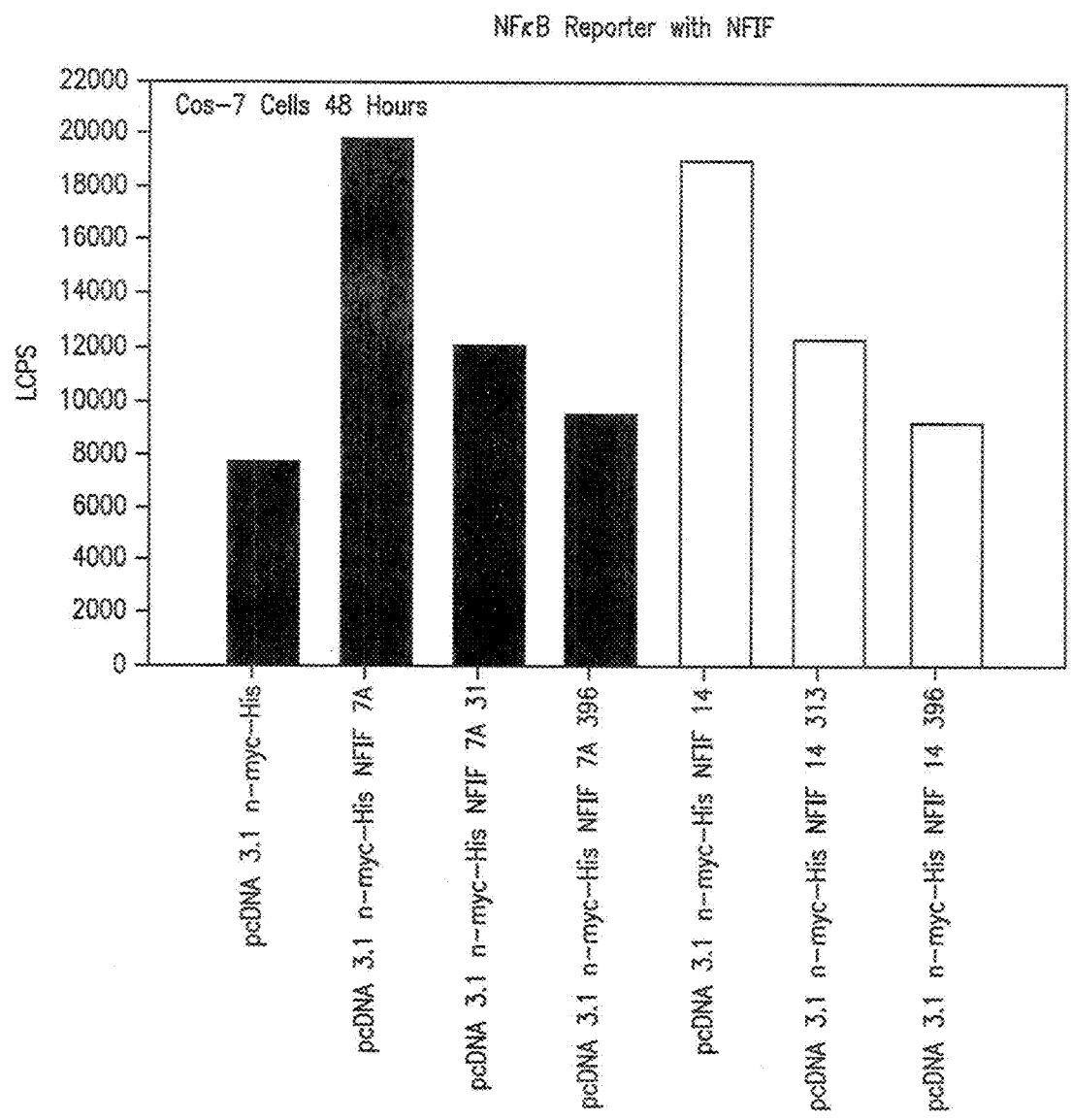
FIG. 6 is a bar graph representing luminometer counts per second observed in Cos-7 cells at 48 hours.

Analysis of the results from 24 hour, 48 hour, 72 hour timepoints identified the 48 hour timepoint as the most optimal for assessing activity. The positive control for the assay was a 24 hour tumor necrosis factor (α) (TNFα) stimulation of the cells one day posttransfection with the pcDNA3.1mychis vector. In HEK293 cells, the full-length pcDNAmychis 7, pcDNAmychis14 cDNAs transient transfections demonstrated luminometer count per second at ~3.1 fold and ~2.1 fold respectively, above vector only (FIG. 5) and in COS-7 cells (FIG. 6) full-length clone pcDNAmychis 7 gave a 2.4 fold signal and pcDNAmychis 14 a 2.3 fold increase in luminometer count per second above vector only. The deletion mutants (pcDNAmychis 7-313, pcDNAmychis 7-396, pcDNAmychis 14-313 and pcDNAmychis 14-396) showed reduced activity. Assays run on other days using the 48 hour timepoint gave variability in response ranging between a 2-5 fold increase for clone 7 (full-length) and 2-4 fold for clone 14.

Example 5

Identification of Tissues Expressing or Containing NFIF Proteins

Figure 8:
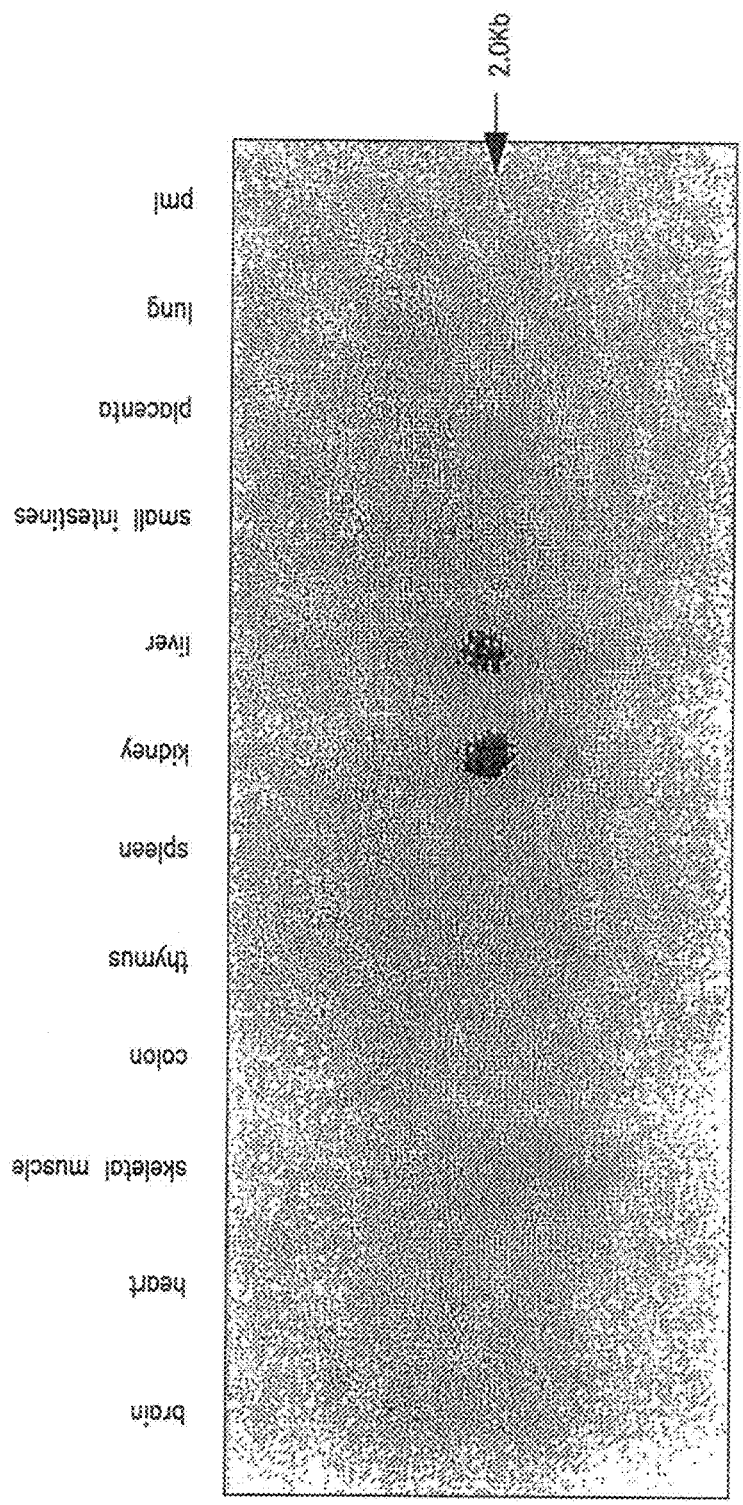
FIG. 8 is a Northern Blot using an NFIF probe.

In order to determine which human tissues express the NFIF proteins, a Clontech pre-made Northern Blot (Human 12 lane #7780-1) was probed with randomly primed p32 labelled probes prepared from NFIF. The results can be seen in FIG. 8. As FIG. 8 illustrates, expression of NFIF is particularly evident in skeletal muscle, kidney, liver and placental tissue.

In order to determine if the NFIF protein was associated with pathologies including atherosclerosis that involve inflammation and to identify tissues that may be treated using the methods of the present invention, an immunocytochemical study was performed using a rabbit monoclonal antibody designated 99-06 directed against a peptide antigen (SKGA-NASNPGPFGDV) (SEQ ID NO.: 5) derived from residues 65 to 79 of the NFIF protein. The peptide was synthesized at the 0.25 mmole scale using a solid phase methodology FMOC (9-fluorenylmethyloxycarbonyl) protection scheme in conjunction with the HOBT/HBTU activation chemistry (Fields et al., *Peptide Research,* 4:95-101 (1991)). An Applied Biosystems 433 Peptide Synthesizer running Applied Biosystems Fast-Moc coupling cycle was used for the synthesis of the peptide.

The peptide was cleaved for 1.5 hours at room temperature using a cleavage reagent of 82.5% trifluoroacetic acid (TFA), 5% phenol, 5% H2O, 5% thioanisole, and 2.5% ethanedithiol (King et al., *Intl. J. Peptide and Protein Research,* 36, 255-266 (1990)). Following cleavage, the peptide was precipitated with tert-butyl ether, washed, then dried for 1 hour under vacuum. The peptide was then solubilized in 0.1% TFA/water and purified using C18 reverse phase HPLC. A purity level of >95% was achieved for the peptide, along with correct MALDI-TOF molecular weight data.

10-30 mg of purified peptide was conjugated to keyhole limpet hemocyanin using 1-ethyl-3-(3-dimethylaminopropyl) carbodiimide (EDC). The preparation was dialyzed against PBS at 4° C. exhaustively. The hapten/carrier preparation was mixed 1:1 with Freunds Complete adjuvant and used to inject rabbits for the production of antisera against the peptide. The 15-residue peptide was used to prepare anti-NFIF antibodies in rabbits using standard methods known in the art. Rabbits were immunized by subcutaneous injection with an emulsion of antigen/complete Freund's adjuvant (50% antigen solution/50% complete Freund's adjuvant). Complete Freund's adjuvant (CFA) was used for the initial immunization because this adjuvant has been used very successfully in producing antibody responses to a diverse range of protein and peptide antigens and the incidence of adverse reactions is minimal to none. The injection schedule described below has been optimized for use with Freund's adjuvant. The area to be injected was shaved in order to permit visual assessment of any reaction to the emulsion. Prior to injection, the injection sites were cleansed with diluted Nolvasan scrub solution. Injection sites were on the back starting between the shoulder blades. The injection sites were widely separated and kept close to the midline to reduce the possibility of the animal scratching at the injection sites. Typically, 100 µl containing 20 µg of antigen were injected in 5 subcutaneous sites per rabbit for a total of 100 µg/rabbit. Subsequent, booster injections were given at 4 week intervals with an emulsion of antigen/incomplete Freund's adjuvant. After six weeks, 5-30 mls of blood was collected to determine the titer of the antibody. If the antibody titer was not sufficient, additional booster injections were given at week intervals and blood samples collected every 2-4 weeks. Prior to each anti-gen injection, the condition of the previous injection sites were evaluated for adverse reactions. Animals giving a positive antibody response were maintained and boosted and bled periodically in order to generate a large stock of antisera.

Antibody titration experiments were conducted with Antibody 99-06 to establish concentrations that yield minimal background and maximum detection of signal. A serial dilution study demonstrated the highest signal-to-noise ratio at a dilution of 1:500 and 1:1,000, and slides incubated with these concentrations of antibody were analyzed by the pathologists. Antibody 99-06 was used as the primary antibody, and the principal detection system consisted of a Vector ABC-AP Kit (AK5002) with a Vector Red substrate kit that produced a fuschia-colored red deposit (SK-5100). Tissues were also stained with a positive control antibody (CD31) directed against the human leukocyte antigen (Stockinger et al., *J. Immunol.,* 145(11):3889-97 (1990)) to ensure that the tissue antigens were preserved and accessible for immunocytochemical analysis. In addition to coronary artery samples, additional tissues that were stained and imaged during Phase II of this study were normal spleen, thymus, and lymph node. Staining was performed in the spleen, thymus and lymph node in order to assist in the identification of inflammatory subsets of cells that expressed this protein.

Within the spleen, thymus, and lymph node, Antibody 99-06 showed strong positive staining within the lymphocytes of the periarterial lymphatic sheath, the cords of Billroth, cortical thymic lymphocytes, germinal center cells in the lymph node, and within vascular endothelium and smooth muscle. Other cell types that stained moderately to strongly positive with this antibody included Schwann cells and cardiac myocytes. The signal was predominantly nuclear in the cell types examined, except for cytoplasmic granularity that was seen within smooth muscle cells, and in macrophages that were filled with cellular debris in regions of plaque or organizing thrombus.

Within normal coronary arteries, the antibody was largely negative in the endothelium of the tunica intima except for occasional cells showing a nuclear signal, and myointimal smooth muscle cells showed faint nuclear signals. Within the tunica media, the antibody was moderately uniformly positive within smooth muscle cells. In the adventitia, the endothelium, vascular smooth muscle and inflammatory cells were moderately positive for staining. The internal and external elastic lamellae were negative for staining Within the minimal atherosclerosis samples, the endothelium showed only occasional faint signals even in that overlying the atheroma. Within the superficial atheroma, the myointimal smooth muscle cells showed only faint signals. In deeper regions of the atheroma, proliferating fibroblastic forms and foamy macrophages showed an increased level of staining. In some samples that showed plaques containing cholesterol and areas of calcification, the smooth muscle cells and foamy histiocytes surrounding the cholesterol-laden plaques and calcified material showed increased levels of staining In the samples of moderate atherosclerosis, the endothelium, both in the tunica intima and in areas of neovascularization, showed increased staining with Antibody 99-06. Inflammatory cells marginating along or subjacent to the endothelium were strongly positive for staining Endothelium lining new vessels was moderately to strongly positive for staining, and in areas, the subendothelial myofibroblasts were less positive than associated endothelium. In general, fibroblastic forms of myointimal cells were much less positive than either proliferating or histiocytic forms of smooth muscle cells. In addition, macrophages associated with cholesterol, calcification, or foamy macrophages within plaques showed an increased level of staining. The smooth muscle of the tunica media was fairly uniformly moderately positive within all samples in which the media was intact, and smooth muscle within adventitial vessels was similarly positive.

In cases of severe atherosclerosis, much of the endothelium lining the tunica intima was either denuded or the residual endothelium was faintly to moderately positive for staining. The plaque-associated inflammatory infiltrate showed very strong positive staining within macrophages and lymphocytes, including within regions of neovascularization. Increased staining was also seen within macrophages and lymphocytes adjacent to or surrounding calcifications and cholesterol and within areas of organizing thrombus. The endothelium lining new vessels was strongly positive in these areas. Increased signal intensity was again seen within the histiocytic and proliferating forms compared to fibroblastic forms of smooth muscle cells. In these cases, inflammatory cells such as a subset of lymphocytes, plasma cells, and macrophages within the adventitia were also strongly positive for staining In late stage areas of severe atherosclerosis with minimal inflammation and quiescent plaques, there was much less staining. In these samples, the endothelium was less intensely positive for staining, although residual lymphocytes and macrophages surrounding calcified material showed positive staining.

Biological Material Useful in Practicing the Invention

A deposit of Human NFκB inducing factor 7a (NFIF-7a) cloned from a human vascular smooth muscle cell cDNA library subcloned into a pCR2.1 plasmid vector and a deposit of Human NFκB inducing factor 14b (NFIF-14b) cloned from a human vascular smooth muscle cell cDNA library subcloned into a pCR2.1 plasmid vector will be made with the American Type Culture Collection. Access to these cultures will be available during pendency of the patent application to one determined by the Commissioner to be entitled thereto under 35 U.S.C. §122 and 37 C.F.R. §1.14.

We claim:

1. An isolated and purified nuclear factor kappa B inducing factor (NFIF) 14b polypeptide which induces nuclear factor kappa B (NFκB) in a patient comprising the amino acid sequence of SEQ ID NO:1.

2. An isolated antibody which specifically binds the NFIF-14b polypeptide of claim 1.

3. A composition comprising the polypeptide of claim 1 and a pharmaceutically acceptable carrier.

4. A composition comprising the antibody of claim 2 and a pharmaceutically acceptable carrier.

5. The composition of claim 3, further comprising a biocompatible solution.

6. A method of increasing expression of NFκB in a patient comprising introducing the composition of claim 3 into the body of the patient.

7. A method of inhibiting inflammation comprising administration of the composition of claim 4 to a patient.

8. An isolated and purified NFIF-14b polypeptide which induces NFκB in a patient comprising the amino acid sequence encoded by nucleotides 394 to 1362 of SEQ ID NO: 3.

9. The NFIF-14b polypeptide of claim 8, further comprising lower NFκB inducing activity than the NFIF-14b polypeptide of claim 1.

* * * * *

SEQUENCE LISTING

```
<160> NUMBER OF SEQ ID NOS: 10

<210> SEQ ID NO 1
<211> LENGTH: 453
<212> TYPE: PRT
<213> ORGANISM: Homo sapiens

<400> SEQUENCE: 1

Met Ala Leu Val Arg Ala Leu Val Cys Cys Leu Leu Thr Ala Trp His
 1               5                  10                  15

Cys Arg Ser Gly Leu Gly Leu Pro Val Ala Pro Ala Gly Gly Arg Asn
            20                  25                  30

Pro Pro Pro Ala Ile Gly Gln Phe Trp His Val Thr Asp Leu His Leu
        35                  40                  45

Asp Pro Thr Tyr His Ile Thr Asp Asp His Thr Lys Val Cys Ala Ser
    50                  55                  60

Ser Lys Gly Ala Asn Ala Ser Asn Pro Gly Pro Phe Gly Asp Val Leu
65                  70                  75                  80

Cys Asp Ser Pro Tyr Gln Leu Ile Leu Ser Ala Phe Asp Phe Ile Lys
                85                  90                  95

Asn Ser Gly Gln Glu Ala Ser Phe Met Ile Trp Thr Gly Asp Ser Pro
            100                 105                 110

Pro His Val Pro Val Pro Glu Leu Ser Thr Asp Thr Val Ile Asn Val
```

```
            115                 120                 125
Ile Thr Asn Met Thr Thr Ile Gln Ser Leu Phe Pro Asn Leu Gln
130                 135                 140

Val Phe Pro Ala Leu Gly Asn His Asp Tyr Trp Pro Gln Asp Gln Leu
145                 150                 155                 160

Ser Val Val Thr Ser Lys Val Tyr Asn Ala Val Ala Asn Leu Trp Lys
                165                 170                 175

Pro Trp Leu Asp Glu Glu Ala Ile Ser Thr Leu Arg Lys Gly Gly Phe
            180                 185                 190

Tyr Ser Gln Lys Val Thr Thr Asn Pro Asn Leu Arg Ile Ile Ser Leu
        195                 200                 205

Asn Thr Asn Leu Tyr Tyr Gly Pro Asn Ile Met Thr Leu Asn Lys Thr
210                 215                 220

Asp Pro Ala Asn Gln Phe Glu Trp Leu Glu Ser Thr Leu Asn Asn Ser
225                 230                 235                 240

Gln Gln Asn Lys Glu Lys Val Tyr Ile Ile Ala His Val Pro Val Gly
                245                 250                 255

Tyr Leu Pro Ser Ser Gln Asn Ile Thr Ala Met Arg Glu Tyr Tyr Asn
            260                 265                 270

Glu Lys Leu Ile Asp Ile Phe Gln Lys Tyr Ser Asp Val Ile Ala Gly
        275                 280                 285

Gln Phe Tyr Gly His Thr His Arg Asp Ser Ile Met Val Leu Ser Asp
290                 295                 300

Lys Lys Gly Ser Pro Val Asn Ser Leu Phe Val Ala Pro Ala Val Thr
305                 310                 315                 320

Pro Val Lys Ser Val Leu Glu Lys Gln Thr Asn Asn Pro Gly Ile Arg
                325                 330                 335

Leu Phe Gln Tyr Asp Pro Arg Asp Tyr Lys Leu Leu Asp Met Leu Gln
            340                 345                 350

Tyr Tyr Leu Asn Leu Thr Glu Ala Asn Leu Lys Gly Glu Ser Ile Trp
        355                 360                 365

Lys Leu Glu Tyr Ile Leu Thr Gln Thr Tyr Asp Ile Glu Asp Leu Gln
370                 375                 380

Pro Glu Ser Leu Tyr Gly Leu Ala Lys Gln Phe Thr Ile Leu Asp Ser
385                 390                 395                 400

Lys Gln Phe Ile Lys Tyr Tyr Asn Tyr Phe Phe Val Ser Tyr Asp Ser
                405                 410                 415

Ser Val Thr Cys Asp Lys Thr Cys Lys Ala Phe Gln Ile Cys Ala Ile
            420                 425                 430

Met Asn Leu Asp Asn Ile Ser Tyr Ala Asp Cys Leu Lys Gln Leu Tyr
        435                 440                 445

Ile Lys His Asn Tyr
450

<210> SEQ ID NO 2
<211> LENGTH: 364
<212> TYPE: PRT
<213> ORGANISM: Homo sapiens

<400> SEQUENCE: 2

Met Ala Leu Val Arg Ala Leu Val Cys Cys Leu Leu Thr Ala Trp His
1               5                   10                  15

Cys Arg Ser Gly Leu Gly Leu Pro Val Ala Pro Ala Gly Gly Arg Asn
            20                  25                  30

Pro Pro Pro Ala Ile Gly Gln Phe Trp His Val Thr Asp Leu His Leu
```

|   |   |   | 35 |   |   |   | 40 |   |   |   | 45 |   |
|---|---|---|----|---|---|---|----|---|---|---|----|---|

Asp Pro Thr Tyr His Ile Thr Asp Asp His Thr Lys Val Cys Ala Ser
   50                    55                   60

Ser Lys Gly Ala Asn Ala Ser Asn Pro Gly Pro Phe Gly Asp Val Leu
65                  70                  75                   80

Cys Asp Ser Pro Tyr Gln Leu Ile Leu Ser Ala Phe Asp Phe Ile Lys
                 85                   90                  95

Asn Ser Gly Gln Glu Ala Ser Phe Met Ile Trp Thr Gly Asp Ser Pro
            100                105              110

Pro His Val Pro Val Pro Glu Leu Ser Thr Asp Thr Val Ile Asn Val
       115                120              125

Ile Thr Asn Met Thr Thr Thr Ile Gln Ser Leu Phe Pro Asn Leu Gln
   130                  135                  140

Val Phe Pro Ala Leu Gly Asn His Asp Tyr Trp Pro Gln Val Tyr Ile
145                 150                155              160

Ile Ala His Val Pro Val Gly Tyr Leu Pro Ser Ser Gln Asn Ile Thr
            165                170              175

Ala Met Arg Glu Tyr Tyr Asn Glu Lys Leu Ile Asp Ile Phe Gln Lys
       180                185              190

Tyr Ser Asp Val Ile Ala Gly Gln Phe Tyr Gly His Thr His Arg Asp
   195                  200                  205

Ser Ile Met Val Leu Ser Asp Lys Lys Gly Ser Pro Val Asn Ser Leu
   210                  215                  220

Phe Val Ala Pro Ala Val Thr Pro Val Lys Ser Val Leu Glu Lys Gln
225                 230                235              240

Thr Asn Asn Pro Gly Ile Arg Leu Phe Gln Tyr Asp Pro Arg Asp Tyr
            245                250              255

Lys Leu Leu Asp Met Leu Gln Tyr Tyr Leu Asn Leu Thr Glu Ala Asn
       260                265              270

Leu Lys Gly Glu Ser Ile Trp Lys Leu Glu Tyr Ile Leu Thr Gln Thr
   275                  280                  285

Tyr Asp Ile Glu Asp Leu Gln Pro Glu Ser Leu Tyr Gly Leu Ala Lys
   290                  295                  300

Gln Phe Thr Ile Leu Asp Ser Lys Gln Phe Ile Lys Tyr Tyr Asn Tyr
305                 310                315              320

Phe Phe Val Ser Tyr Asp Ser Ser Val Thr Cys Asp Lys Thr Cys Lys
            325                330              335

Ala Phe Gln Ile Cys Ala Ile Met Asn Leu Asp Asn Ile Ser Tyr Ala
       340                345              350

Asp Cys Leu Lys Gln Leu Tyr Ile Lys His Asn Tyr
   355                  360

<210> SEQ ID NO 3
<211> LENGTH: 1362
<212> TYPE: DNA
<213> ORGANISM: Homo sapiens

<400> SEQUENCE: 3
atggcgctgg tgcgcgcact cgtctgctgc ctgctgactg cctggcactg ccgctccggc     60
ctcgggctgc ccgtggcgcc cgcaggcggc aggaatcctc ctccggcgat aggacagttt    120
tggcatgtga ctgacttaca cttagaccct acttaccaca tcacagatga ccacacaaaa    180
gtgtgtgctt catctaaagg tgcaaatgcc tccaaccctg gcccttttgg agatgttctg    240
tgtgattctc catatcaact tattttgtca gcatttgatt ttattaaaaa ttctggacaa    300

```
gaagcatctt tcatgatatg gacagggat  agcccacctc atgttcctgt acctgaactc    360
tcaacagaca ctgttataaa tgtgatcact aatatgacaa ccaccatcca gagtctcttt    420
ccaaatctcc aggttttccc tgcgctgggt aatcatgact attggccaca ggatcaactg    480
tctgtagtca ccagtaaagt gtacaatgca gtagcaaacc tctggaaacc atggctagat    540
gaagaagcta ttagtacttt aaggaaaggt ggttttttatt cacagaaagt tacaactaat    600
ccaaacctta ggatcatcag tctaaacaca aacttgtact acggcccaaa tataatgaca    660
ctgaacaaga ctgacccagc caaccagttt gaatggctag aaagtacatt gaacaactct    720
cagcagaata aggagaaggt gtatatcata gcacatgttc cagtggggta tctgccatct    780
tcacagaaca tcacagcaat gagagaatac tataatgaga aattgataga tattttttcaa    840 aaatacagtg atgtcattgc aggacaattt tatggacaca ctcacagaga cagcattatg    900
gttctttcag ataaaaaagg aagtccagta aattctttgt tgtggctcc  tgctgttaca    960 ccagtgaaga gtgttttaga aaacagacc  aacaatcctg gatcagact  gtttcagtat   1020 gatcctcgtg attataaatt attggatatg ttgcagtatt acttgaatct gacagaggcg   1080
aatctaaagg gagagtccat ctggaagctg agtatatcc  tgacccagac ctacgacatt   1140
gaagatttgc agccggaaag tttatatgga ttagctaaac aatttacaat cctagacagt   1200
aagcagttta taaatacta  caattacttc tttgtgagtt atgacagcag tgtaacatgt   1260
gataagacat gtaaggcctt tcagatttgt gcaattatga atcttgataa tatttcctat   1320
gcagattgcc tcaaacagct ttatataaag cacaattact ag                      1362

<210> SEQ ID NO 4
<211> LENGTH: 1095
<212> TYPE: DNA
<213> ORGANISM: Homo sapiens

<400> SEQUENCE: 4
atggcgctgg tgcgcgcact cgtctgctgc ctgctgactg cctggcactg ccgctccggc     60
ctcgggctgc ccgtggcgcc cgcaggcggc aggaatcctc ctccggcgat aggacagttt    120
tggcatgtga ctgacttaca cttagaccct acttaccaca tcacagatga ccacacaaaa    180
gtgtgtgctt catctaaagg tgcaaatgcc tccaaccctg gccctttttgg agatgttctg    240 tgtgattctc catatcaact tatttttgtca gcatttgatt ttattaaaaa ttctggacaa    300
gaagcatctt tcatgatatg gacagggat  agcccacctc atgttcctgt acctgaactc    360
tcaacagaca ctgttataaa tgtgatcact aatatgacaa ccaccatcca gagtctcttt    420
ccaaatctcc aggttttccc tgcgctgggt aatcatgact attggccaca ggtgtatatc    480
atagcacatg ttccagtggg gtatctgcca tcttcacaga acatcacagc aatgagagaa    540
tactataatg agaaattgat agatattttt caaaagtaca gtgatgtcat tgcaggacaa    600
ttttatggac acactcacag agacagcatt atggttcttt cagataaaaa aggaagtcca    660
gtaaattctt tgtttgtggc tcctgctgtt acaccagtga gagtgtttt  agaaaaacag    720 accaacaatc ctggtatcag actgtttcag tatgatcctc gtgattataa attattggat    780
atgttgcagt attacttgaa tctgacagag gcgaatctaa agggagagtc catctggaag    840
ctggagtata tcctgaccca gacctacgac attgaagatt tgcagccgga agtttatat    900 ggattagcta aacaatttac aatcctagac agtaagcagt ttataaaata ctacaattac    960
ttctttgtga gttatgacag cagtgtaaca tgtgataaga catgtaaggc ctttcagatt   1020
tgtgcaatta tgaatcttga taatatttcc tatgcagatt gcctcaaaca gctttatata   1080
```

```
aagcacaatt actag                                                    1095
```

<210> SEQ ID NO 5
<211> LENGTH: 15
<212> TYPE: PRT
<213> ORGANISM: Homo sapiens

<400> SEQUENCE: 5

Ser Lys Gly Ala Asn Ala Ser Asn Pro Gly Pro Phe Gly Asp Val
 1               5                  10                  15

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Based on
      NFIF-14b and NFIF-7a but with Kozak sequence 5' to
      ATG

<400> SEQUENCE: 6

```
tccaccatgg cgctggtgcg cgcactc                                         27
```

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Based on
      NFIF-14b and NFIF-7a but with an EcoRV site added
      onto the end

<400> SEQUENCE: 7

```
gtcgaaatat atttcgtgtt aatgctatag gtc                                  33
```

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Based on
      NFIF-14b and NFIF-7a but with Kozak sequence 5' to
      ATG

<400> SEQUENCE: 8

```
gctccaccat gatatggaca ggggatag                                        28
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Based on
      NFIF-14b and NFIF-7a but with an EcoRV site added
      onto the end

<400> SEQUENCE: 9

```
gccactgtgc tggatatcgt aattaac                                         27
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Based on
      NFIF-14b and NFIF-7a but with Kozak sequence 5' to
      ATG -continued

```
<400> SEQUENCE: 10
gctccaccat gacaaccacc atccagagtc                                            30
```